(12) United States Patent
Ascher et al.

(10) Patent No.: US 11,813,416 B2
(45) Date of Patent: Nov. 14, 2023

(54) CATHETER SYSTEMS AND METHODS FOR PERFORMING A DESTRUCTION OF A BODY OBSTRUCTION

(71) Applicant: HEXACATH, Rueil-Malmaison (FR)

(72) Inventors: Gilles Ascher, Neuilly-sur-Seine (FR); Bernard De Bruyne, Kraainem (BE); Nico Pijls, Waalre (NL)

(73) Assignee: HEXACATH, Rueil-Malmaison (FR)

( * ) Notice: Subject to any disclaimer, the term of this patent is extended or adjusted under 35 U.S.C. 154(b) by 675 days.

(21) Appl. No.: 16/897,347

(22) Filed: Jun. 10, 2020

(65) Prior Publication Data

US 2020/0316348 A1 Oct. 8, 2020

Related U.S. Application Data

(63) Continuation-in-part of application No. 14/261,139, filed on Apr. 24, 2014, now Pat. No. 10,716,482.

(Continued)

(51) Int. Cl.
*A61M 25/09* (2006.01)
*A61M 25/00* (2006.01)
(Continued)

(52) U.S. Cl.
CPC ............ *A61M 25/09* (2013.01); *A61B 5/028* (2013.01); *A61B 5/6852* (2013.01);
(Continued)

(58) Field of Classification Search
CPC .... A61B 2562/0247; A61B 2562/0271; A61B 5/028; A61B 5/6852; A61B 17/22;
(Continued)

(56) References Cited

U.S. PATENT DOCUMENTS 3,545,428 A 12/1970 Webster
3,620,207 A 11/1971 Sinclair
(Continued)

FOREIGN PATENT DOCUMENTS

EP 1930045 6/2008
NL 1 034 242 8/2008
(Continued)

OTHER PUBLICATIONS

Kenneth O. Hill et al., "Fiber Bragg Grating Technology Fundamentals and Overview", Journal of Lightwave Technology, vol. 15, No. 8, Aug. 1997.
(Continued)

*Primary Examiner* — Eric J Messersmith
(74) *Attorney, Agent, or Firm* — Clark & Brody LP

(57) ABSTRACT

A catheter system and a method for performing body obstruction destruction are disclosed. The catheter comprises a catheter shaft comprising a proximal end and a distal end, including an outer tubular member and at least one inner tubular member disposed within the outer tubular member; a first fluid lumen defined between the inner tubular member and the outer tubular member and at least one second lumen defined by the inner tubular member; one or more fluid exit openings located at a distal end region of the catheter configured to permit fluid to exit the catheter from the first fluid lumen; fluid pressure means located external of the catheter ahead from the proximal end for delivering said fluid in the first fluid lumen at a pressure range predetermined to cause destruction of said obstruction.

36 Claims, 20 Drawing Sheets

Related U.S. Application Data

(60) Provisional application No. 61/816,022, filed on Apr. 25, 2013.

(51) Int. Cl.
  *A61B 5/028* (2006.01)
  *A61B 5/00* (2006.01)
  *A61M 25/01* (2006.01)

(52) U.S. Cl.
  CPC ............... *A61B 2562/0247* (2013.01); *A61B 2562/0271* (2013.01); *A61M 2025/0001* (2013.01); *A61M 2025/018* (2013.01); *A61M 2025/09008* (2013.01); *A61M 2205/3334* (2013.01); *A61M 2205/3368* (2013.01)

(58) Field of Classification Search
  CPC .... A61B 17/32037; A61B 2017/00088; A61B 2017/00092; A61B 2017/22042; A61B 2017/22062; A61B 2017/22084; A61B 5/015; A61B 5/4836; A61M 2025/0001; A61M 2025/018; A61M 2025/09008; A61M 2205/3334; A61M 2205/3368; A61M 25/09; A61M 2025/0183; A61M 2025/1086; A61M 25/007
  See application file for complete search history.

(56) References Cited

U.S. PATENT DOCUMENTS

| | | | |
|---|---|---|---|
| 3,726,269 A | | 4/1973 | Webster |
| 4,153,048 A | | 5/1979 | Magrini |
| 4,576,182 A | | 3/1986 | Normann |
| 5,178,153 A | | 1/1993 | Einzig |
| 5,281,203 A | | 1/1994 | Ressemann |
| 5,370,609 A | * | 12/1994 | Drasler ............ A61B 17/32037 606/128 |
| 5,766,194 A | * | 6/1998 | Smith ................ A61B 17/3203 606/1 |
| 6,231,498 B1 | | 5/2001 | Pfeiffer et al. |
| 6,343,514 B1 | | 2/2002 | Smith |
| 6,485,500 B1 | | 11/2002 | Kokish et al. |
| 6,551,250 B2 | | 4/2003 | Khalil |
| 6,623,436 B2 | | 9/2003 | Krivitski et al. |
| 6,635,027 B1 | | 10/2003 | Cragg et al. |
| 7,112,176 B2 | | 9/2006 | Krivitski et al. |
| 7,549,965 B2 | | 6/2009 | Krivitski et al. |
| 7,572,244 B2 | * | 8/2009 | Weisel ................ A61B 17/22 604/93.01 |
| 7,775,988 B2 | | 8/2010 | Pijls |
| 8,133,185 B2 | | 3/2012 | Krivitski et al. |
| 2002/0177783 A1 | | 11/2002 | Khalil |
| 2003/0158490 A1 | | 8/2003 | Krivitski et al. |
| 2003/0158491 A1 | | 8/2003 | Krivitski et al. |
| 2004/0054293 A1 | | 3/2004 | Krivitski et al. |
| 2005/0113798 A1 | | 5/2005 | Slater et al. |
| 2006/0200191 A1 | * | 9/2006 | Zadno-Azizi ...... A61M 25/1011 604/101.05 |
| 2007/0078352 A1 | | 4/2007 | Pijls |
| 2008/0161840 A1 | * | 7/2008 | Osiroff ............. A61B 17/32037 606/159 |
| 2009/0171267 A1 | | 7/2009 | Bonnette et al. |
| 2010/0286537 A1 | | 11/2010 | Pijls |
| 2011/0208072 A1 | | 8/2011 | Pfeiffer et al. |
| 2012/0238869 A1 | | 9/2012 | Schmitt et al. |
| 2014/0081134 A1 | | 3/2014 | Fortson et al. |
| 2014/0276602 A1 | * | 9/2014 | Bonnette .......... A61B 17/32037 604/151 |
| 2014/0277006 A1 | * | 9/2014 | Bonnette .......... A61B 17/32037 606/159 |
| 2014/0323887 A1 | | 10/2014 | Anderson et al. |
| 2017/0354427 A1 | | 12/2017 | Bonnette et al. |

FOREIGN PATENT DOCUMENTS

| | | |
|---|---|---|
| WO | 2009/049823 | 4/2009 |
| WO | 2012/164481 | 12/2012 |

OTHER PUBLICATIONS

Marcel Van't Veer et al., "Continuous infusion thermodilusion for assessment of coronary flow: Theoretical background and in vitro validation", Medical Engineering and Physics, Jan. 25, 2009.

Wilbert Aarnoudse et al., "Direct Volumetric Blood Flow Measurement in Coronary Arteries by Thermodilution", Journal of American College of Cardiology, Dec. 7, 2007.

\* cited by examiner

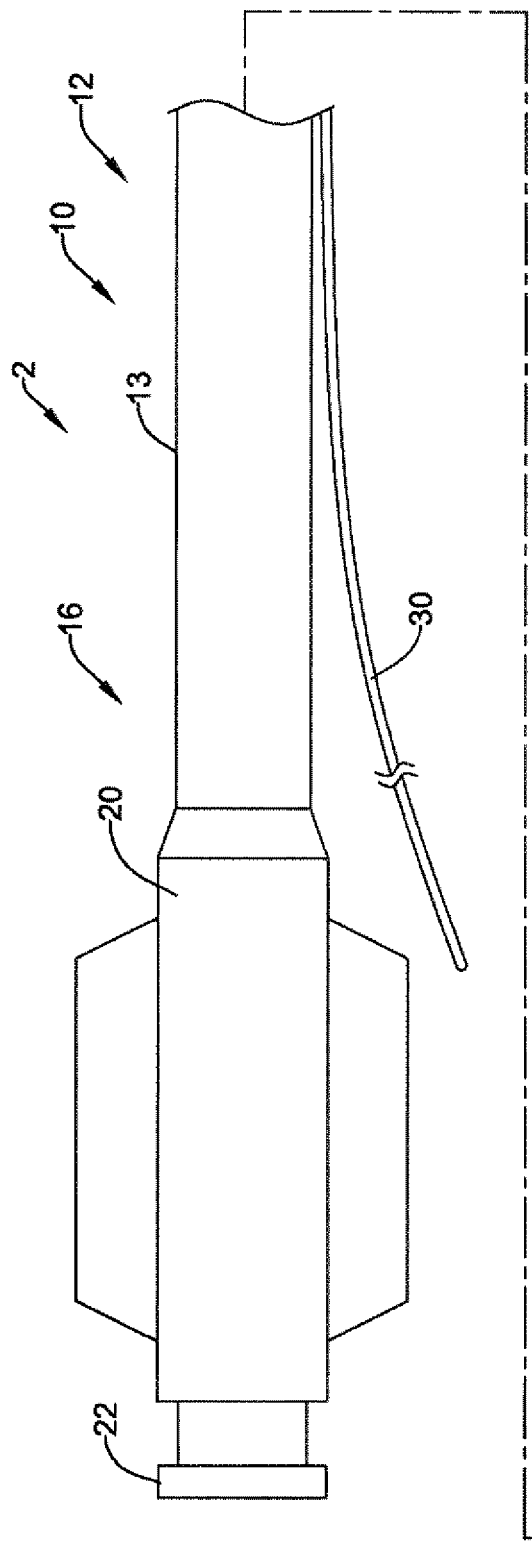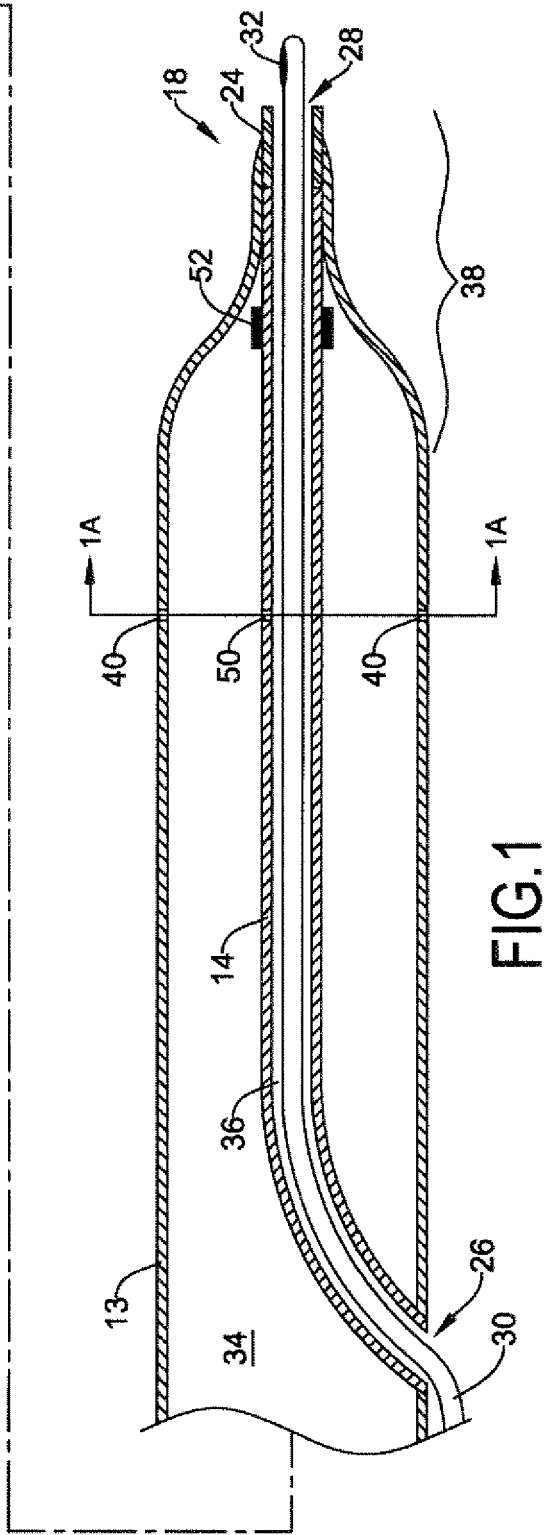
FIG.1

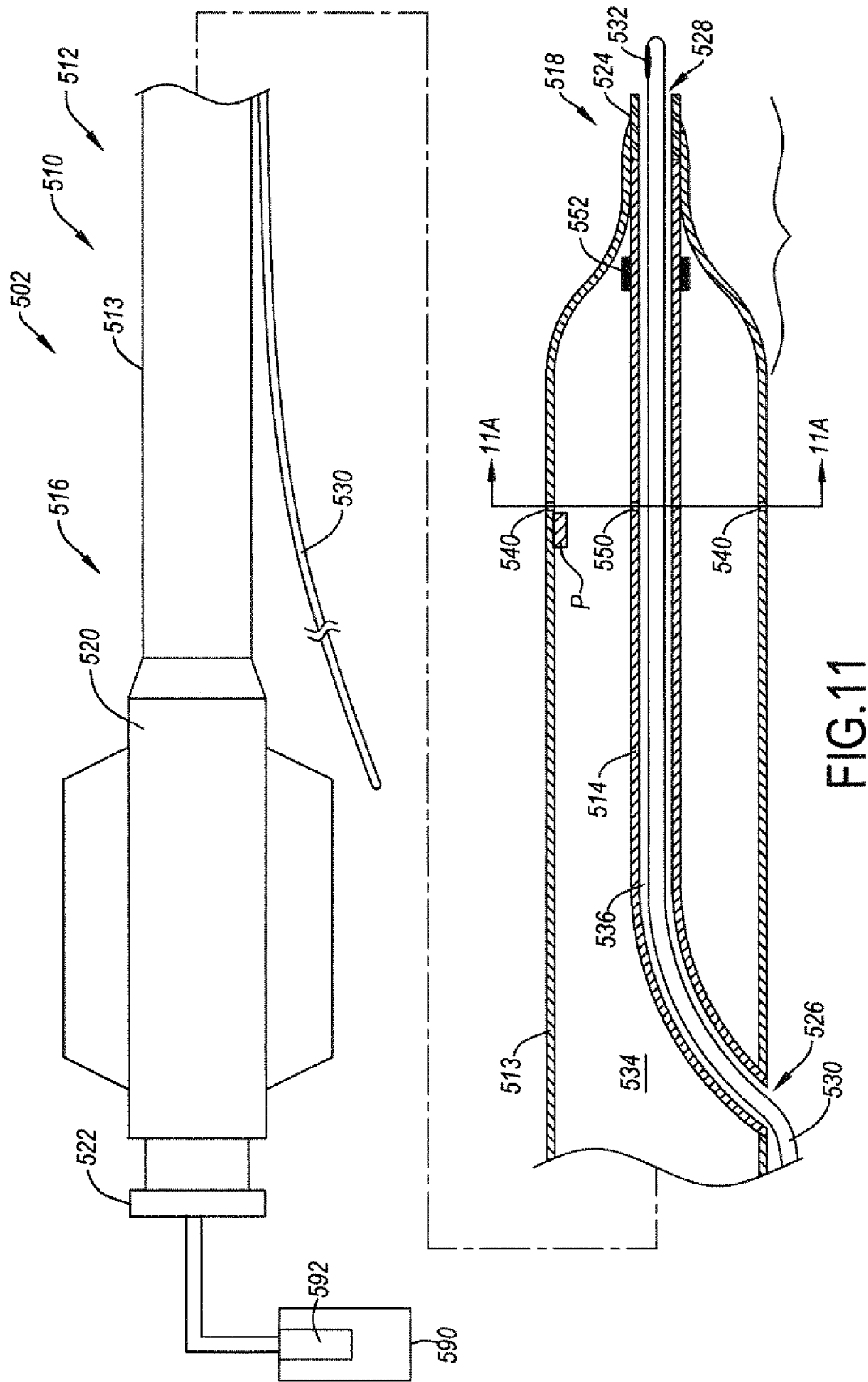

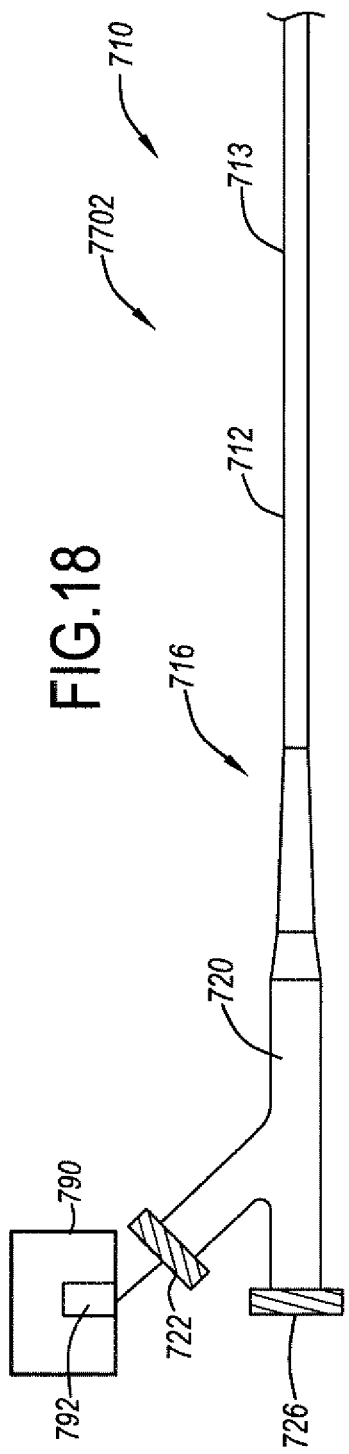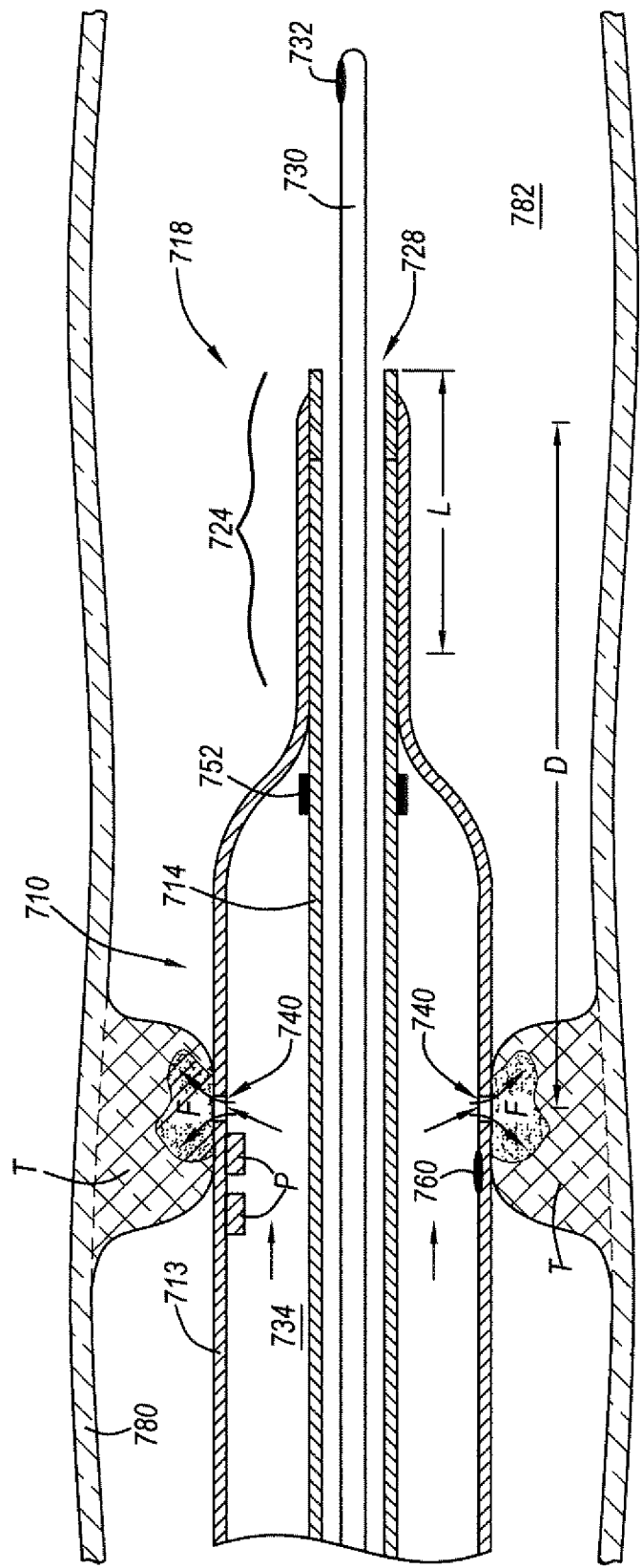
FIG.18

CATHETER SYSTEMS AND METHODS FOR PERFORMING A DESTRUCTION OF A BODY OBSTRUCTION

CROSS-REFERENCE TO RELATED APPLICATIONS

This application is a Continuation in Part from pending U.S. patent application Ser. No. 14/261,139 filed on Apr. 24, 2014, published as US 2014/0323887 on Oct. 30, 2014, which claims priority under 35 U.S.C. § 119 to U.S. Provisional Application Ser. No. 61/816,022, filed Apr. 25, 2013, the entirety of which is incorporated herein by reference.

TECHNICAL FIELD

The disclosure is directed to catheter systems for having both a thermodilution action and a body obstruction destruction action, and methods for determining blood flow rates and for performing body obstruction destruction.

BACKGROUND

Thermodilution is a method of determining blood flow through a body vessel based on in vivo measurements of temperature drop of blood using a temperature sensor as a result of introducing an indicator fluid (e.g., saline) having a lower temperature than blood into the blood upstream from the temperature sensor. The measured temperature drop, which is a function of the blood flow and set indicator fluid flow, may be used to determine the absolute blood flow rate through the body vessel. The calculated absolute blood flow rate may be used for the diagnosis and understanding of microvascular disease.

Accordingly, there is a need to provide alternative systems and methods for determining the absolute blood flow rate in blood vessels, such as coronary arteries.

Further, there is a need for destructing body obstructions, particularly in body vessels, arteries, coronaries, like thrombus, thrombosis and blood clots.

SUMMARY

The disclosure is directed to several alternative designs, materials and methods of manufacturing medical device structures and assemblies, and uses thereof.

Accordingly, one illustrative embodiment is a catheter system for determining blood flow in a body lumen. The system includes a catheter including an outer tubular member and an inner tubular member disposed within the outer tubular member. The catheter also includes a fluid lumen defined between the inner tubular member and the outer tubular member and a second lumen (e.g., a guidewire lumen, a temperature probe lumen, etc.) defined by the inner tubular member. One or more fluid infusion openings are located at a distal end region of the catheter. The one or more fluid infusion openings are configured to permit fluid to exit the catheter from the fluid lumen. Additionally, one or more fluid holes are located at the distal end region of the catheter, and are configured to permit fluid to pass from the fluid lumen into the second lumen. In some instances, the catheter system also includes an elongate member (e.g., a guidewire, a temperature probe, etc.) advanceable through the second lumen of the catheter. The elongate member may include a temperature sensor positioned on a distal end portion of the elongate member which is positionable within the second lumen of the inner tubular member to measure a temperature of fluid entering the second lumen of the inner tubular member through the one or more fluid holes.

Another illustrative embodiment is a catheter system for determining blood flow in a body lumen. The system includes an elongate catheter shaft having a proximal end, a distal end, and a lumen extending therethrough. The catheter shaft also includes one or more fluid infusion openings located at a distal end region of the catheter shaft. The one or more fluid infusion openings are configured to permit fluid to exit the lumen of the catheter shaft into the body lumen. A first temperature sensor is positioned within the lumen of the catheter shaft proximate the one or more fluid infusion openings. The first temperature sensor is configured to be in direct contact with a fluid within the lumen to measure a temperature of the fluid exiting the lumen through the one or more fluid infusion openings. In some instances, the elongate catheter shaft may include an elongated reduced diameter region extending distal of the one or more fluid infusion openings to the distal end of the elongate catheter shaft. A second temperature sensor may be positioned on an exterior of the elongated reduced diameter region proximate the distal end of the elongate catheter shaft to measure a mixture of blood and fluid infused into the blood from the catheter shaft.

Yet another illustrative embodiment is a method of determining blood flow in a body vessel of a patient. The method includes advancing a catheter to a desired location within the body vessel. The catheter includes an outer tubular member, an inner tubular member disposed within the outer tubular member, a fluid lumen defined between the inner tubular member and the outer tubular member, and a second lumen defined by the inner tubular member. A fluid is delivered through the fluid lumen to a distal end region of the catheter. A temperature sensor mounted on an elongate member is positioned within the second lumen of the catheter and the temperature of the fluid passing into the second lumen from the fluid lumen is measured with the temperature sensor positioned in the second lumen. The fluid is infused into blood in the body vessel from the fluid lumen and the temperature of a mixture of the fluid and the blood is measured with a temperature sensor mounted on an elongate member positioned in the body vessel distal of the catheter. The blood flow rate may then be calculated based on the measured temperature of the fluid and the measured temperature of the mixture of the fluid and the blood.

A still further illustrative embodiment is a catheter system for performing body obstruction destruction in a live being body lumen, for example a blood vessel. By the terms blood vessel in this specification and claims, it is meant any blood vessel in which blood flows, including a vessel, an artery, a coronary, etc. The live being may be a human or an animal. The body obstruction may be a thrombus or thrombosis, or a blood clot.

According to a particular embodiment, the invention further relates to a catheter system for performing destruction of a body obstruction in a body vessel of a live being, comprising a catheter shaft comprising a proximal end and a distal end, including an outer tubular member and at least one inner tubular member disposed within the outer tubular member; a first fluid lumen defined between the inner tubular member and the outer tubular member and at least one second lumen defined by the at least one inner tubular member; one or more fluid exit openings located at a distal end region of the catheter configured to permit fluid to exit the catheter from the first fluid lumen; fluid pressure means located external of the catheter ahead from the proximal end for delivering said fluid in the first fluid lumen at a pressure range predetermined to cause destruction of said obstruction.

According to a variant embodiment, the catheter system further comprises an elongate member advanceable through the second lumen of the catheter.

According to a variant feature, the elongate member comprises a temperature sensor positioned on a distal end portion of the elongate member.

According to another variant feature, the temperature sensor on the distal end portion of the elongate member is positionable ahead of the distal end of the catheter to measure temperature in the blood vessel.

According to a variant embodiment, the one or more fluid exit openings extend through a wall of the outer tubular member from an inner surface of the outer tubular member to an outer surface of the outer tubular member.

According to a variant feature, the one or more fluid exit openings are configured to generate a jet of fluid exiting the catheter and at a pressure sufficient to cause mechanical destruction of the body obstruction.

According to a further variant feature, the one or more fluid exit openings include at least one set of four fluid exit openings equidistantly spaced circumferentially around the outer tubular member.

According to another variant feature, the one or more fluid exit openings include at least two sets of four fluid exit openings equidistantly spaced circumferentially around the outer tubular member.

According to another variant embodiment, the fluid exit opening(s) have a diameter ranging between about 50 microns (0.050 millimeters) and about 110 microns (0.110 millimeters). The diameter size selected is usually adapted to the pressure of the fluid and said fluid pressure at the entrance of said catheter or at the vicinity of at least one fluid exit opening ranges between about 20×101,325 Pa or 20 ATM and about 50×101,325 Pa or 50 ATM.

According to a variant embodiment, the fluid exit opening(s) have a diameter ranging between about 70 microns (0.070 millimeters) and about 100 microns (0.100 millimeters).

According to a further variant embodiment, the pressure of the fluid at the entrance of said catheter or at the vicinity of at least one fluid exit opening ranges between at least, or more than, 30×101,325 Pa or 30 ATM and 50×101,325 Pa or 50 ATM. This pressure is particularly adapted with a size of the orifices ranging between about 70 microns (0.070 millimeters) and about 100 microns (0.100 millimeters)

According to a variant embodiment, one or more fluid holes are located at the distal end region of the catheter, and are configured to permit fluid to pass from the first fluid lumen into the second lumen and said one or more fluid holes extend through a wall of the inner tubular member from an outer surface of the inner tubular member to an inner surface of the inner tubular member.

According to a variant feature, the one or more fluid holes are one or more weeping holes configured to allow fluid to weep into the second lumen.

According to a further variant feature, the one or more fluid holes have a diameter ranging between about, or more than, 100 micrometers and about 300 micrometers.

According to a variant embodiment, the elongate catheter shaft includes an elongated reduced diameter region extending distal of the one or more fluid exit openings to the distal end of the elongate catheter shaft.

According to another variant embodiment, a first temperature sensor is positioned within the first fluid lumen of the catheter shaft proximate the one or more fluid exit openings, the first temperature sensor configured to be in direct contact with the fluid within the lumen to measure a temperature of the fluid exiting the lumen through the one or more fluid exit openings.

According to another variant feature, the catheter further comprises a second temperature sensor positioned on an exterior of the elongated reduced diameter region proximate the distal end of the elongate catheter shaft.

According to a variant feature, the second temperature sensor is positioned at least 4 centimeters distal of the one or more fluid exit openings.

According to another variant feature, the distal end of the inner tubular member is sealingly secured to the distal end of the elongate catheter shaft.

According to a further variant feature, an elongate member comprises a guidewire advanceable through the inner tubular member.

According to a variant embodiment, the guidewire comprises a temperature sensor positioned on a distal end portion of the guidewire to measure a temperature of a blood/fluid mixture in the body lumen distal of the one or more fluid exit openings.

According to another variant embodiment, the catheter comprises at least one pressure sensor in the vicinity of at least one fluid exit opening.

According to a further variant embodiment, the fluid is a liquid selected from a saline and an aqueous solution compatible with blood comprising at least one clot or thrombosis dissolution aid.

According to another variant feature, said elongate member is a guidewire, and wherein said catheter is selected from an Over The Wire (OTW) catheter and a Single Operator Exchange (SOE) catheter.

According to a further aspect, the invention relates to a method of performing destruction of a body obstruction in a body vessel of a live being, the method comprising:

advancing a catheter to a desired location within the body vessel, the catheter including a catheter shaft comprising a proximal end and a distal end, comprising an outer tubular member and at least one inner tubular member disposed within the outer tubular member; a first fluid lumen defined between the inner tubular member and the outer tubular member and at least one second lumen defined by the inner tubular member; one or more fluid exit openings located at a distal end region of the catheter configured to permit fluid to exit the catheter from the first fluid lumen;

providing a delivery of a fluid through the first fluid lumen to a distal end region of the catheter and at a pressure range predetermined to exit said fluid at a pressure and for a period of time causing destruction of said obstruction.

According to a variant embodiment, the catheter comprises at least one set of four fluid exit openings located at the distal end region of the catheter equidistantly spaced circumferentially around the outer tubular member.

According to a further variant embodiment, the catheter comprises two sets of four fluid exit openings located at the distal end region of the catheter equidistantly spaced circumferentially around the outer tubular member.

According to a variant feature, the advancing step of said catheter within said body step comprises using an elongate member.

According to another variant feature, said elongate member is a guidewire, and wherein said catheter is selected from an Over The Wire (OTW) catheter and a Single Operator Exchange (SOE) catheter.

According to another variant embodiment, said catheter is provided with a temperature sensor, said method comprising measuring with said temperature sensor the temperature of the fluid exiting the catheter or of the blood ahead of the distal end of the catheter.

According to a variant embodiment, the method is further comprising:

providing at least one temperature sensor on the distal end of the elongate member and positioning the elongate member to a location distal of the catheter for measuring the temperature of the mixture of the fluid and the blood distal of the catheter.

According to another variant embodiment, the catheter includes one or more fluid holes located at the distal end region of the catheter in the vicinity of at least one said fluid exit opening, the one or more fluid holes configured on the inner tube to permit the fluid to pass from the first fluid lumen into the second lumen; and repositioning the elongate member to a location in front of one said fluid hole to measure the temperature of the fluid in the vicinity of the fluid exiting the catheter.

According to another variant embodiment, the fluid exit opening(s) have a diameter ranging between about 50 microns (0.050 millimeters) and about 110 microns (0.110 millimeters). The diameter size selected is usually adapted to the pressure of the fluid and said fluid pressure at the entrance of said catheter or at the vicinity of at least one fluid exit opening ranges between about 20×101,325 Pa or 20 ATM and about 50×101,325 Pa or 50 ATM.

According to a variant embodiment, the fluid exit opening(s) have a diameter ranging between about 70 microns (0.070 millimeters) and about 100 microns (0.100 millimeters).

According to a further variant embodiment, the pressure of the fluid at the entrance of said catheter or at the vicinity of at least one fluid exit opening ranges between at least, or more than, 30×101,325 Pa or 30 ATM and 50×101,325 Pa or 50 ATM. This pressure is particularly adapted with a size of the orifices ranging between about 70 microns (0.070 millimeters) and about 100 microns (0.100 millimeters).

The period of time required to achieve the full, or substantially the full, destruction of the obstruction depends of course from the type and the volume of obstruction. Said period of time generally varies between a few seconds and a few minutes, in particular between about 30 seconds and about 5 minutes.

According to another variant embodiment, the catheter comprises at least one pressure sensor in the vicinity of at least one fluid exit opening and the method comprises measuring the pressure at the vicinity of said fluid exit opening and correcting the pressure value of the fluid injected into said fluid lumen.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 1 is a schematic representation of an exemplary catheter system including an infusion catheter and associated guidewire for determining blood flow through a body vessel using a thermodilution technique;

FIG. 11 is a schematic representation of an exemplary further catheter system including a catheter and associated guidewire for performing destruction of a body obstruction, for instance a thrombus, through a body vessel of a live being, let it be a human or an animal.

FIG. 18 is a schematic representation of another embodiment of a catheter system for performing destruction of a body obstruction, for instance a blood clot, through a body vessel of a live being, let it be a human or an animal.

Figure 1A:
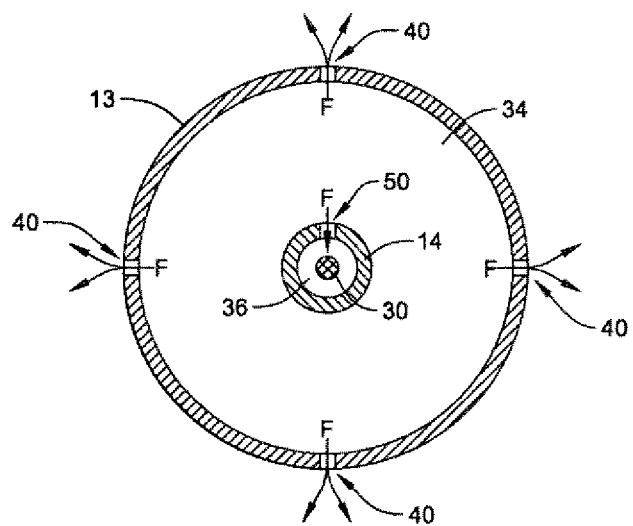
FIG. 1A is a cross-sectional view taken along line 1A-1A of FIG. 1.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

A body vessel should be understood as meaning any vessel in a live being wherein blood flows, including a vessel, an artery, a coronary, etc. A live being may be a human and an animal. An obstruction in a body or blood vessel may be any obstruction, for instance a thrombus, a thrombosis, or a blood clot, without any limitation.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary catheter system 2 including an infusion catheter 10 and associated guidewire 30 for determining blood flow through a body vessel using a thermodilution technique is illustrated in FIG. 1. The infusion catheter 10 may include an elongate catheter shaft 12 extending distally from a hub assembly 20. The catheter shaft 12 may have a proximal end 16 attached to the hub assembly 20 and a distal end 18 opposite the proximal end 16. The catheter shaft 12 may be a dual lumen catheter shaft having a first, infusion fluid lumen 34 and a second, guidewire lumen 36 extending along at least a portion of the catheter shaft 12 configured for advancing the infusion catheter 10 over a guidewire 30. For example, in some embodiments, the catheter 10 may be an over-the-wire (OTW) catheter in which the guidewire lumen 36 may extend through the entire length of the catheter shaft 12 from the distal end 18 to the proximal end 16. However, in other embodiments, such as the embodiment shown in FIG. 1, the catheter 10 may be a single-operator-exchange (SOE) catheter in which the guidewire lumen 36 extends only through a distal portion of the catheter shaft 12.

The catheter shaft 12 may include an outer tubular member 13 and an inner tubular member 14 extending through the lumen of the outer tubular member 13. With the SOE catheter construction of FIG. 1, the infusion fluid lumen 34 may be defined by the outer tubular member 13 through the proximal portion of the catheter shaft 12, while the infusion fluid lumen 34 may be defined between an outer surface of the inner tubular member 14 and an inner surface of the outer tubular member 13 through the distal portion of the catheter shaft 12. In embodiments in which the catheter is an OTW construction, the infusion fluid lumen 34 may be defined between an outer surface of the inner tubular member 14 and an inner surface of the outer tubular member 13 throughout the catheter shaft 12. The hub assembly 20 may include a proximal port 22 in fluid communication with the infusion fluid lumen 34. A source of infusion fluid (not shown), such as an infusion pump, syringe, etc., may be coupled to the proximal port 22 to supply infusion fluid to the infusion fluid lumen 34.

The lumen of the inner tubular member 14 may define the guidewire lumen 36 with a distal guidewire port 28 proximate the distal end of the inner tubular member 14 and a proximal guidewire port 26 proximate the proximal end of the inner tubular member 14. The distal guidewire port 28 may be located proximate the distal end 18 of the catheter shaft 12 and the proximal guidewire port 26 may be located a short distance proximal of the distal end 18 and distal of the proximal end 16 of the catheter shaft 12. The proximal guidewire port 26 may be of any desired construction, providing access to the guidewire lumen 36. For example, in some embodiments the proximal guidewire port 26 may be formed in accordance with a guidewire port forming process as described in U.S. Pat. No. 6,409,863, which is incorporated herein by reference.

A distal end portion 38 of the outer tubular member 13 may be a reduced diameter portion or necked portion, secured to the inner tubular member 14 to seal the infusion lumen 34 proximate the distal end 18 of the catheter shaft 12. For example, the distal end portion 38 may include a tapered region in which the outer tubular member 13 tapers down to a reduced inner and/or outer diameter at the distal end of the outer tubular member 13. Thus, the inner surface of a distal end portion of the outer tubular member 13 may be secured to the outer surface of a distal end portion of the inner tubular member 14 in the distal end portion 38. The outer tubular member 13 may be secured to the inner tubular member 14, for example, by laser welding, hot jaws, or other thermal bonding method, an adhesive bonding method, or other bonding method if desired.

In some instances, the catheter shaft 12 may include a distal tip 24, formed as a separate component and secured at the distal end 18 of the catheter shaft 12. For example, in some instances the distal tip 24 may be secured to the inner tubular member 14 and/or outer tubular member 13, for example, by laser welding, hot jaws, or other thermal bonding method, an adhesive bonding method, or other bonding method if desired. As shown in FIG. 1, in some embodiments, the distal end portion of the outer tubular member 13 may span the joint between the inner tubular member 14 and the distal tip 24 such that the distal end portion of the outer tubular member 13 is bonded to each of the inner tubular member 14 and the distal tip 24. In other instances, the distal tip 24 may be formed as a unitary portion of the inner tubular member 14 and/or the outer tubular member 13.

The catheter shaft 12 may also include one or more radiopaque markers 52 located proximate the distal end 18 of the catheter shaft 12. The radiopaque marker(s) 52 may facilitate viewing the location of the distal end 18 of the catheter shaft 12 using a fluoroscopy technique or other visualization technique during a medical procedure. In the illustrative embodiment, the catheter shaft 12 includes a radiopaque marker 52 secured to the inner tubular member 14 proximate the tapered distal end portion 38 of the catheter shaft 12.

The catheter shaft 12 may include one or more fluid infusion openings 40 (e.g., holes, apertures) located at a distal end region of the catheter 10. The fluid infusion openings 40 may be in fluid communication with the infusion fluid lumen 34 and may be configured to permit infusion fluid to exit the catheter 10 from the infusion fluid lumen 34 proximate the distal end 18 of the catheter shaft 12. For example, the catheter shaft 12 may include a plurality of fluid infusion openings 40 extending through a wall of the outer tubular member 13 from an inner surface of the outer tubular member 13 to an outer surface of the outer tubular member 13. As shown in FIG. 1A, in one illustrative embodiment, the catheter shaft 12 may include four fluid infusion openings 40 equidistantly spaced circumferentially around the outer tubular member 13 (i.e., with each fluid infusion opening 40 arranged about 90° from another fluid infusion opening 40. In other embodiments, the catheter shaft 12 may include one, two, three, or more fluid infusion openings 40 arranged around the perimeter of the catheter shaft 12.

The fluid infusion openings 40 may be configured to expel an infusion fluid (e.g., an indicator fluid) in a radially outward direction from each of the fluid infusion openings 40 to facilitate mixing of the infusion fluid with blood flowing through the vessel lumen. In other embodiments, the fluid infusion openings 40 may be arranged in a different orientation, such as in a fashion to permit infusion fluid to be expelled generally distally from the catheter shaft 12, if desired.

Figure 2:
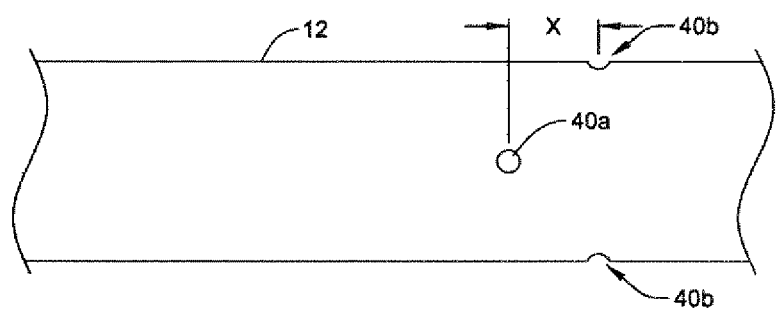
FIG. 2 is a side view of a portion of the infusion catheter of FIG. 1.

As shown in FIG. 2, in some instances one or more of the fluid infusion openings 40 may be longitudinally displaced from one or more of the other fluid infusion openings 40. For example, first and second oppositely positioned fluid infusion openings 40a (only one of which is visible in FIG. 2) may be located a longitudinal distance X, such as about 0.5 millimeters, about 1 millimeter, about 2 millimeters, or about 3 millimeters, away from third and fourth oppositely positioned fluid infusion openings 40b, in some embodiments. In other embodiments, the first and second oppositely positioned fluid infusion openings 40a may be longitudinally aligned with the third and fourth oppositely positioned fluid infusion openings 40b, if desired.

The one or more fluid infusion openings 40 may be configured to generate a jet of infusion fluid F exiting the catheter shaft 12. For example, the fluid infusion openings 40 may be appropriately sized to generate a pressure stream of the infusion fluid F exiting the fluid infusion openings 40. In some instances, the fluid infusion openings 40 may have a diameter of about 25 microns (0.025 millimeters) to about 300 microns (0.300 millimeters), about 25 microns (0.025 millimeters) to about 100 microns (0.100 millimeters), about 100 microns (0.100 millimeters) to about 200 microns (0.200 millimeters), or about 200 microns (0.200 millimeters) to about 300 microns (0.300 millimeters), for example. The size of the fluid infusion openings 40 may be selected based on the volume of infusion fluid to ensure a jet of infusion fluid is formed exiting the catheter shaft 12.

The catheter shaft 12 may also include one or more fluid holes 50 (e.g., openings, apertures) located at the distal end region of the catheter 10. The fluid hole(s) 50 may be in fluid communication with the infusion fluid lumen 34 and may be configured to permit infusion fluid to pass from the infusion fluid lumen 34 into the guidewire lumen 36. For example, the catheter shaft 12 may include one or more fluid holes 50 extending through a wall of the inner tubular member 14 from an outer surface of the inner tubular member 14 to an inner surface of the inner tubular member 14. As shown in FIG. 1A, in the illustrative embodiment the catheter shaft 12 may include one fluid hole 50 extending through the wall of the inner tubular member 14 to permit infusion fluid F to enter the guidewire lumen 36 from the infusion fluid lumen 34. However, in other embodiments the catheter shaft 12 may include two, three or more such fluid holes 50, if desired.

The fluid hole(s) 50 may be a weeping hole configured to allow infusion fluid to weep or exude slowly into the guidewire lumen 36 from the infusion fluid lumen 34. For instance, the fluid hole(s) 50 may be configured to allow infusion fluid to weep, drip, trickle, ooze or otherwise slowly exude into the guidewire lumen 36. In some instances, the fluid hole(s) 50 may have a diameter of about 100 microns (0.100 millimeters) to about 300 microns (0.300 millimeters), about 100 microns (0.100 millimeters) to about 200 microns (0.200 millimeters), or about 200 microns (0.200 millimeters) to about 300 microns (0.300 millimeters), for example.

The catheter system 2 may also include an elongate member, such as a guidewire 30 sized and configured to be disposed through the guidewire lumen 36 of the infusion catheter 10 such that the infusion catheter 10 may be advanced along the guidewire 30 to a target location in the vasculature. The guidewire 30 may include a temperature sensor 32, such as a thermistor or a thermocouple, mounted on a distal end region of the guidewire 30. One illustrative embodiment of a guidewire 30 having a temperature sensor 32 mounted thereon is described in U.S. Pat. No. 6,343,514, which is incorporated by reference herein. In some instances, the guidewire 30 may also include a pressure sensor located at the distal end region of the guidewire 30 for measuring blood pressure at a target location within the vasculature.

Figure 3:
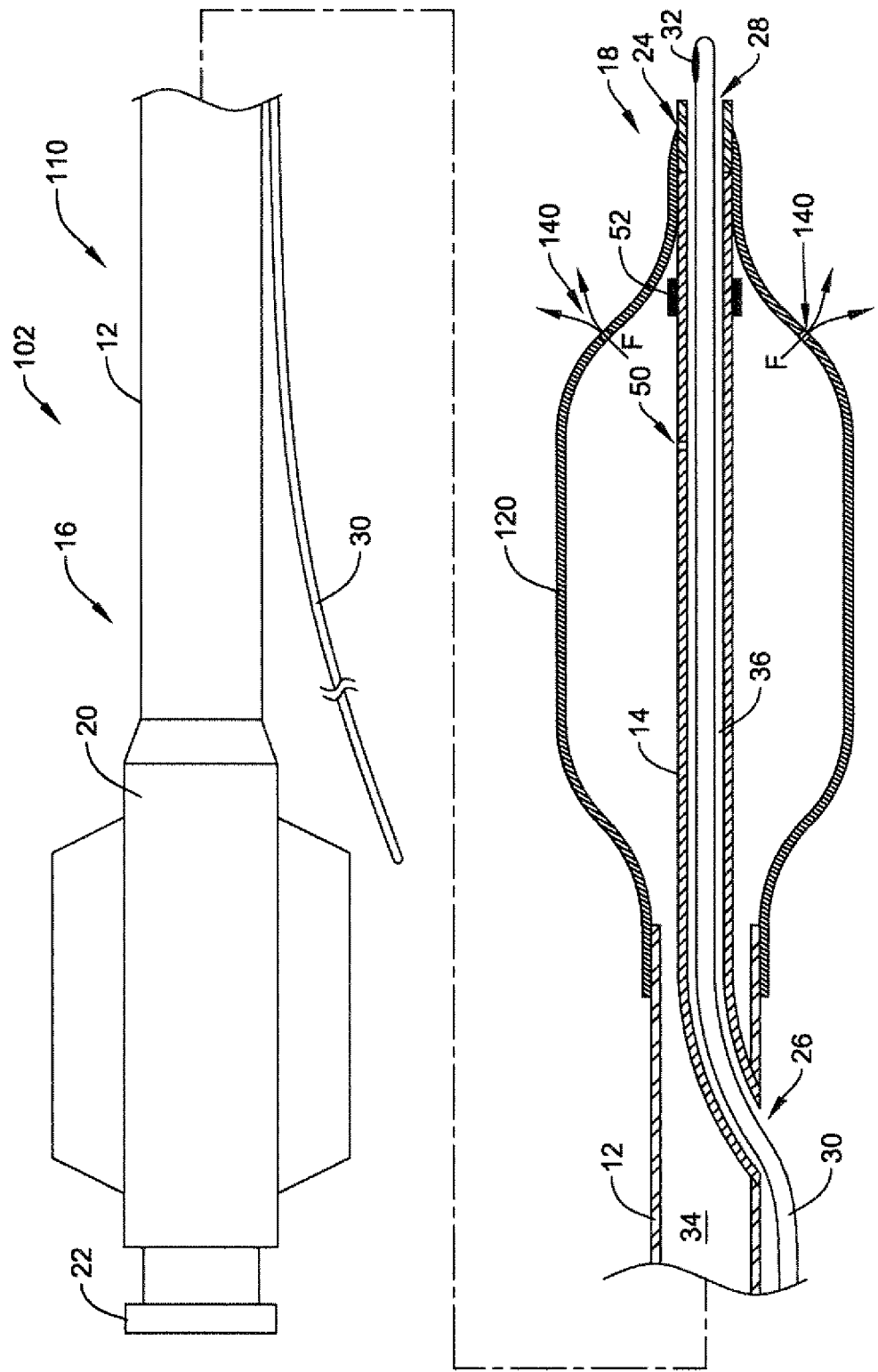
FIG. 3 is a schematic representation of an alternative embodiment of a catheter system including an infusion catheter and associated guidewire for determining blood flow through a body vessel using a thermodilution technique.

Another illustrative catheter system 102 including an infusion catheter 110 and associated guidewire 30 for determining blood flow through a body vessel using a thermodilution technique is illustrated in FIG. 3. In many respects the infusion catheter 110 may be similar to the infusion catheter 10 illustrated in FIG. 1. For example, the infusion catheter 110 may include an elongate catheter shaft 12 extending distally from a hub assembly 20, having a proximal end 16 attached to the hub assembly 20 and a distal end 18 opposite the proximal end 16. The catheter shaft 12 may be a dual lumen catheter shaft having a first, infusion fluid lumen 34 and a second, guidewire lumen 36 extending along at least a portion of the catheter shaft 12 configured for advancing the infusion catheter 110 over the guidewire 30.

The catheter shaft 12 may include an outer tubular member 13 and an inner tubular member 14 extending through the lumen of the outer tubular member 13. With the SOE catheter construction of FIG. 3, the infusion fluid lumen 34 may be defined by the outer tubular member 13 through the proximal portion of the catheter shaft 12, while the infusion fluid lumen 34 may be defined between an outer surface of the inner tubular member 14 and an inner surface of the outer tubular member 13 through the distal portion of the catheter shaft 12. In embodiments in which the catheter is an OTW construction, the infusion fluid lumen 34 may be defined between an outer surface of the inner tubular member 14 and an inner surface of the outer tubular member 13 throughout the catheter shaft 12. The hub assembly 20 may include a proximal port 22 in fluid communication with the infusion fluid lumen 34. A source of infusion fluid (not shown), such as an infusion pump, syringe, etc., may be coupled to the proximal port 22 to supply infusion fluid to the infusion fluid lumen 34.

The lumen of the inner tubular member 14 may define the guidewire lumen 36 with a distal guidewire port 28 proximate the distal end of the inner tubular member 14 and a proximal guidewire port 26 proximate the proximal end of the inner tubular member 14.

The catheter 110 may include an inflatable balloon 120 mounted on a distal region of the catheter shaft 12. For example, the inflatable balloon 120 may include a proximal balloon waist secured (e.g., thermally or adhesively bonded) to a distal end of the outer tubular member 13 and a distal balloon waist secured (e.g., thermally or adhesively bonded) to a distal end of the inner tubular member 14. The infusion fluid lumen 34 extending along the catheter shaft 12 may be in fluid communication with the interior of the inflatable balloon 120 to delivery infusion fluid to the inflatable balloon 120.

The inflatable balloon 120 may include one or more fluid infusion openings 140 (e.g., holes, apertures) configured to permit infusion fluid to exit the balloon 120 from the infusion fluid lumen 34. For example, the balloon 120 may include a plurality of fluid infusion openings 140 extending through a wall of the balloon 120 when the balloon 120 is inflated with the infusion fluid. In one illustrative embodiment, the balloon 120 may include four fluid infusion openings 140 equidistantly spaced circumferentially around the balloon 120 (i.e., with each fluid infusion opening 140 arranged about 90° from another fluid infusion opening 140). In other embodiments, the balloon 120 may include one, two, three, or more fluid infusion openings 140 arranged around the perimeter of the balloon 120.

The fluid infusion openings 140 may be configured to expel an infusion fluid radially outward from the balloon 120 to facilitate mixing of the infusion fluid with blood flowing through the vessel lumen. For example, the fluid infusion openings 140 may be located on the distal cone portion of the balloon 120, on a cylindrical body portion of the balloon 120, or at a different position, if desired. In some instances, the balloon may be configured to create turbulence in the blood flow to facilitate mixing the infusion fluid with the blood flowing distal of the balloon 120.

The fluid infusion openings 140 may be configured to generate a jet of infusion fluid exiting the balloon 120. For example, the fluid infusion openings 140 may be appropriately sized to generate a pressure stream of the infusion fluid exiting the fluid infusion openings 140. The size of the fluid infusion openings 140 may be selected based on the volume of infusion fluid to ensure a jet of infusion fluid is formed exiting the balloon 120.

Similar to the infusion catheter 10, the catheter shaft 12 of the infusion catheter 110 may also include one or more fluid holes 50 (e.g., openings, apertures) located at the distal end region of the catheter 110 configured to permit infusion fluid to pass from the infusion fluid lumen 34 into the guidewire lumen 36. For example, the catheter shaft 12 may include one or more fluid holes 50 extending through a wall of the inner tubular member 14 from an outer surface of the inner tubular member 14 to an inner surface of the inner tubular member 14. The fluid hole(s) 50 may be a weeping hole configured to allow infusion fluid to weep or exude slowly into the guidewire lumen 36 from the infusion fluid lumen 34. For instance, the fluid hole(s) 50 may be configured to allow infusion fluid to weep, drip, trickle, ooze or otherwise slowly exude into the guidewire lumen 36.

Figure 4:
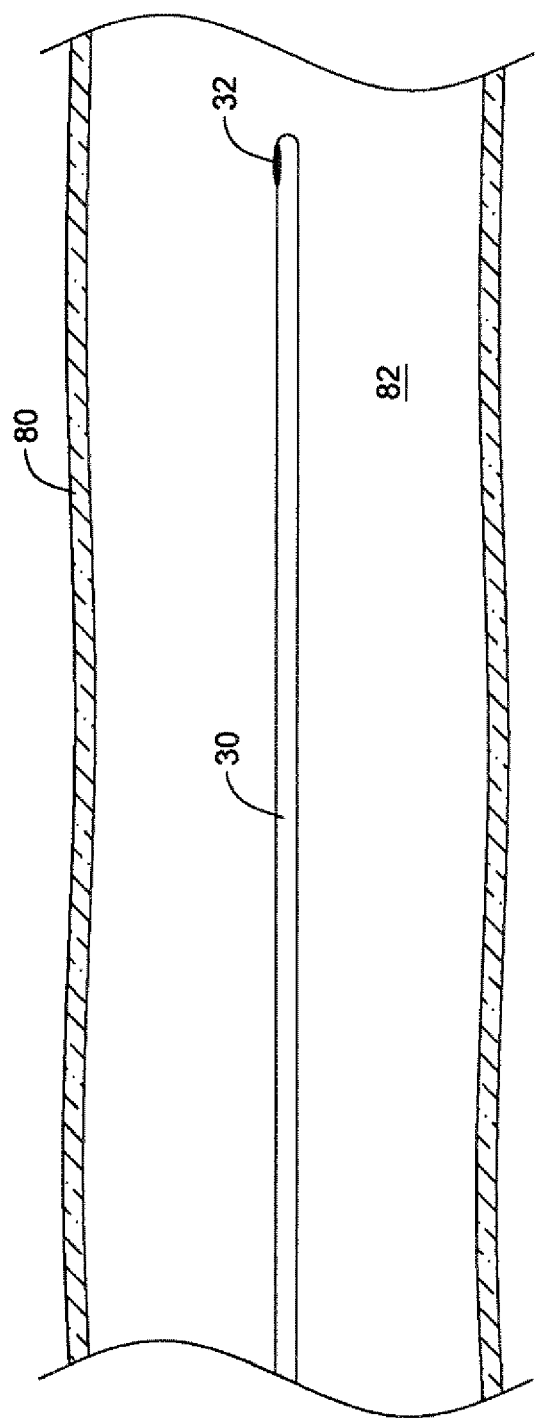
FIGS. 4-7 illustrate aspects of an exemplary method of determining blood flow through a body vessel using the catheter system of FIG. 1.

FIGS. 4-7 illustrate aspects of an exemplary method of determining blood flow through a body vessel using the catheter system of FIG. 1. As shown in FIG. 4, a guidewire, such as the guidewire 30 having a temperature sensor 32 mounted on a distal end region thereof, may be advanced through a lumen 82 of a blood vessel 80 of the vasculature to a desired target location, such as in a coronary artery, for example.

Figure 5:
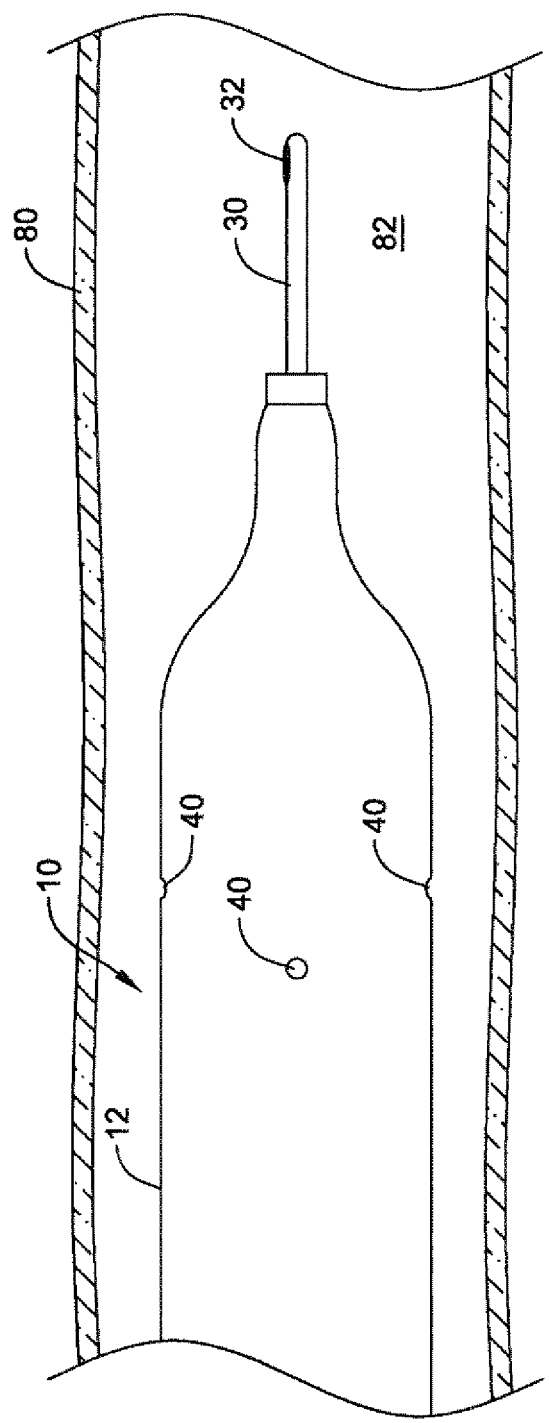

The infusion catheter 10 may then be advanced over the guidewire 30 to the target location within the blood vessel 80, as shown in FIG. 5. In other embodiments, the infusion catheter 10 may be advanced over a different guidewire, such as a conventional guidewire, to the target location, and subsequently the guidewire may be exchanged for the guidewire 30 having a temperature sensor 32 mounted thereon.

With the temperature sensor 32 positioned distal of the infusion catheter 10 the actual temperature $T_b$ of the blood may be measured with the temperature sensor 32 and recorded. In other instances, an estimated temperature (e.g., 98.6° F.) may be used as the temperature $T_b$ of the blood for subsequent calculations.

Figure 6:
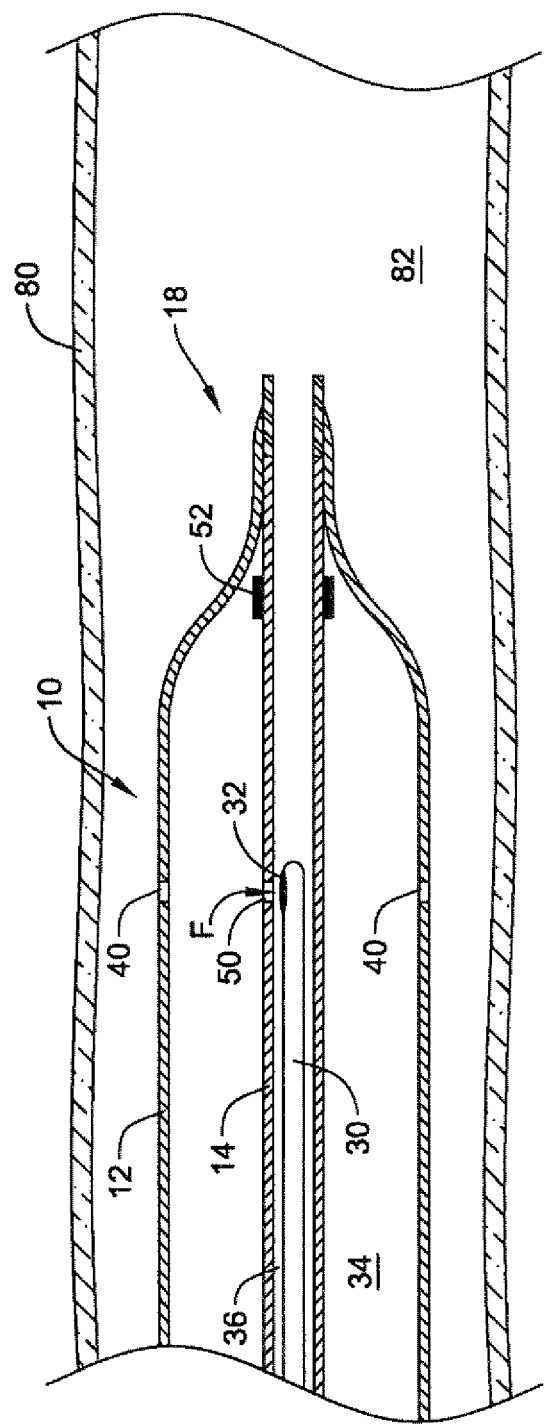

The guidewire 30 may be withdrawn proximally to reposition the sensor 32 inside the guidewire lumen 36, as shown in FIG. 6. For example, the sensor 32 may be positioned within the guidewire lumen 36 adjacent to the fluid hole 50 extending through the inner tubular member 14. The infusion fluid F (e.g., saline) may be delivered through the infusion fluid lumen 34 to the distal end region of the catheter 10. For example, the infusion fluid F may be provided to the distal region of the catheter 10 at a pressure of about 1 ATM to about 30 ATM. A small amount of the infusion fluid F may enter the guidewire lumen 36 through the fluid hole(s) 50 from the infusion fluid lumen 34. Accordingly, with the temperature sensor 32 positioned in the guidewire lumen 36, the actual temperature $T_f$ of the infusion fluid F at the distal end region of the catheter 10 may be measured and recorded. For example, the temperature sensor 32 may be positioned adjacent to the fluid hole(s) 50 such that infusion fluid F passing into the guidewire lumen 36 may come into direct contact with the temperature sensor 32 in the guidewire lumen 36. In other instances, the temperature sensor 32 may be otherwise positioned within the guidewire lumen 36 such that infusion fluid F located in the guidewire lumen 36 may come into direct contact with the temperature sensor 32 in the guidewire lumen 36.

Figure 7:
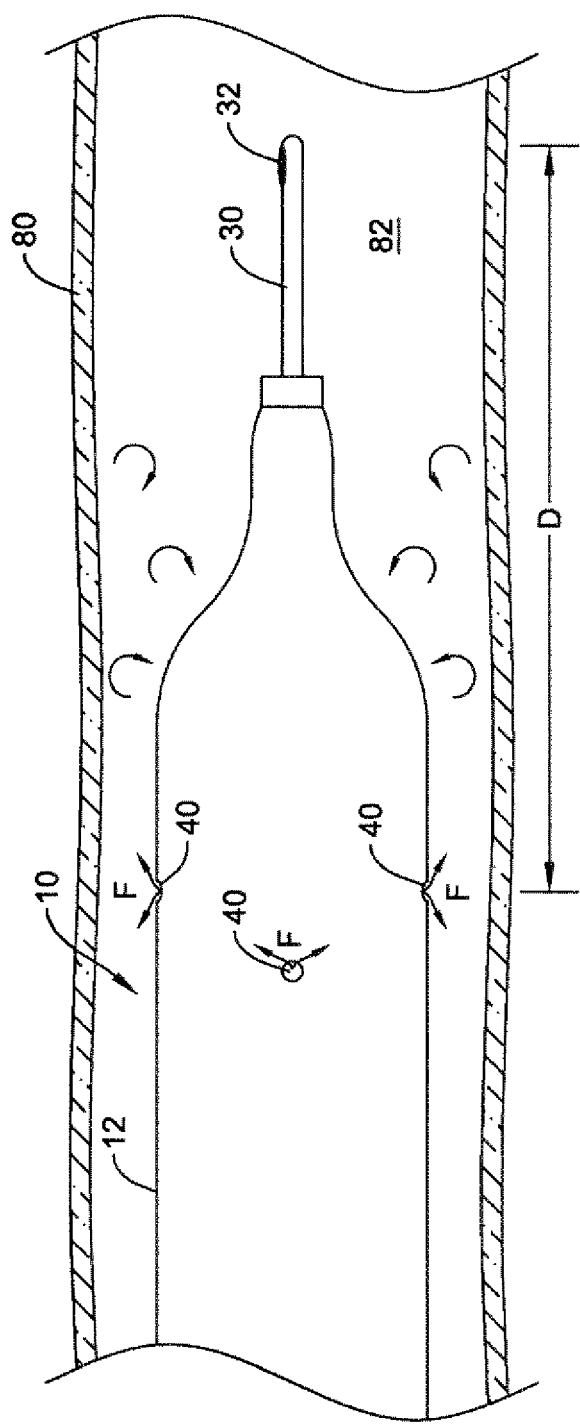

The temperature sensor 32 on the guidewire 30 may then be advanced to a location distal of the catheter 10, as shown in FIG. 7. For example, the temperature sensor 32 may be advanced distally to a position located a distance D from the fluid infusion openings 40. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 32. For example, the temperature sensor 32 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 40 on the catheter shaft 12.

The infusion fluid F may be infused into the blood stream in the lumen 82 of the blood vessel 80 through the fluid infusion openings 40 from the infusion fluid lumen 34. For example, a continuous flow of infusion fluid F at a known flow rate through the infusion fluid lumen 34 may be provided with an infusion pump, with a substantial portion of the infusion fluid F exiting the catheter 10 through the infusion fluid lumen(s) 40 and a small amount of the infusion fluid F exiting the catheter 10 via the guidewire lumen 36. The flow rate of the infusion fluid F may be set to any desired flow rate, for example, a continuous flow rate of about 15 ml/min, about 20 ml/min, about 25 ml/min, about 30 ml/min, about 35 ml/min, or about 40 ml/min. The infusion fluid F may mix with the blood flowing through the blood vessel 80 to provide a mixture of blood and infusion fluid F. If the temperature $T_f$ of the infusion fluid F (e.g., at room temperature) is less than the temperature $T_b$ of the blood, then the mixture of blood and infusion fluid F may have a temperature $T_m$ less than the temperature $T_b$ of the blood.

With the temperature sensor 32 positioned a distance D distal of the infusion fluid opening(s) 40, the temperature $T_m$ of the mixture of blood and infusion fluid F may be measured with the temperature sensor 32 and recorded.

Multiple temperature measurements of the infusion fluid, blood and/or the mixture of blood and infusion fluid may be taken to calculate an average, or adjusted temperature for calculating the blood flow rate through the blood vessel 80.

It is noted that in some instances the temperatures may be measured in any desired order. For example, the temperature $T_m$ of the mixture of the infusion fluid and the blood may be measured first with the temperature sensor 32 located a distance D distal of the catheter 10 as shown in FIG. 7, and then the temperature $T_f$ of the infusion fluid entering the guidewire lumen 36 may be measured by withdrawing the temperature sensor 32 into the guidewire lumen 36 as shown in FIG. 6.

Although a single temperature sensor 32 is illustrated for measuring the temperature $T_f$ of the fluid F, the temperature $T_b$ of the blood, and the temperature $T_m$ of the mixture of blood and infusion fluid, in some instances, the temperature $T_f$ of the fluid F, the temperature $T_b$ of the blood, and/or the temperature $T_m$ of the mixture of blood and infusion fluid may be measured using a different temperature sensor positioned on the guidewire 30 distinct from the temperature sensor 32, a temperature sensor positioned on a second guidewire, positioned on the catheter 10, or otherwise positioned to take the corresponding temperature.

It is noted that the patient with normally be brought to a state of hyperemia, prior to taking the temperature measurements. The measured temperatures may then be used to calculate the actual, absolute blood flow rate of blood in the blood vessel 80 at the target location. For instance, the blood flow rate, which is based on the measured temperature $T_b$ of the blood and the measured temperature $T_m$ of the mixture of the fluid and the blood, may be calculated using the following equation:

$$Q_b = Q_f \times (T_f - T_b)/(T_m - T_b)$$

Where:
$Q_b$=the actual blood flow rate
$Q_f$=the flow rate of the infusion fluid
$T_f$=the temperature of the infusion fluid
$T_b$=the temperature of the blood
$T_m$=the temperature of the mixture of blood and infusion fluid Accordingly, the actual, absolute flow rate of the blood through the blood vessel 80 at the target location may be calculated. The absolute blood flow rate may be used in a diagnostic evaluation for determining a medical condition of the patient. Furthermore, the calculated absolute blood flow rate could be combined with other measurements to provide further diagnostic analysis. For example, the calculated absolute blood flow rate may be combined with an absolute blood pressure measured at the target location in the blood vessel 80 to determine the absolute resistance of the blood vessel 80.

In some instances, the fractional flow reserve (FFR) may be used to measure the pressure drop across a stenosis or narrowing in the blood vessel 80. Fractional flow reserve (FFR) may be calculated with the following equation:

$$FFR = P_d/P_p$$

Where:
$P_d$=measured pressure distal of the stenosis
$P_p$=measured pressure proximal of the stenosis Having calculated the FFR based on the measured pressures proximal and distal to the stenosis or narrowing, and the absolute flow rate of the blood through the blood vessel proximate the stenosis or narrowing, one can calculate the normal maximum flow rate through the blood vessel with the following equation:

$$FFR = Q_b/Q_n$$

Where:
$Q_b$=the actual blood flow rate
$Q_n$=the normal maximum flow rate

When the flow rate of the blood has been calculated and the pressures proximal and distal of the stenosis have been calculated, the resistance of the stenosis or narrowing of the blood vessel 80 can be calculated with the following equation:

$$R_s = (P_p - P_d)/Q_b$$

Where:
$R_s$=resistance across the stenosis or narrowing
$P_d$=measured pressure distal of the stenosis or narrowing
$P_p$=measured pressure proximal of the stenosis or narrowing
$Q_b$=the actual blood flow rate Thus, the measured actual blood flow rate, as well as other calculated parameters, may be useful for the diagnosis and understanding of a number of pathophysiological conditions such as heart transplantation, stem cell therapy, or a transmural myocardial infarction, for example.

Figure 8:
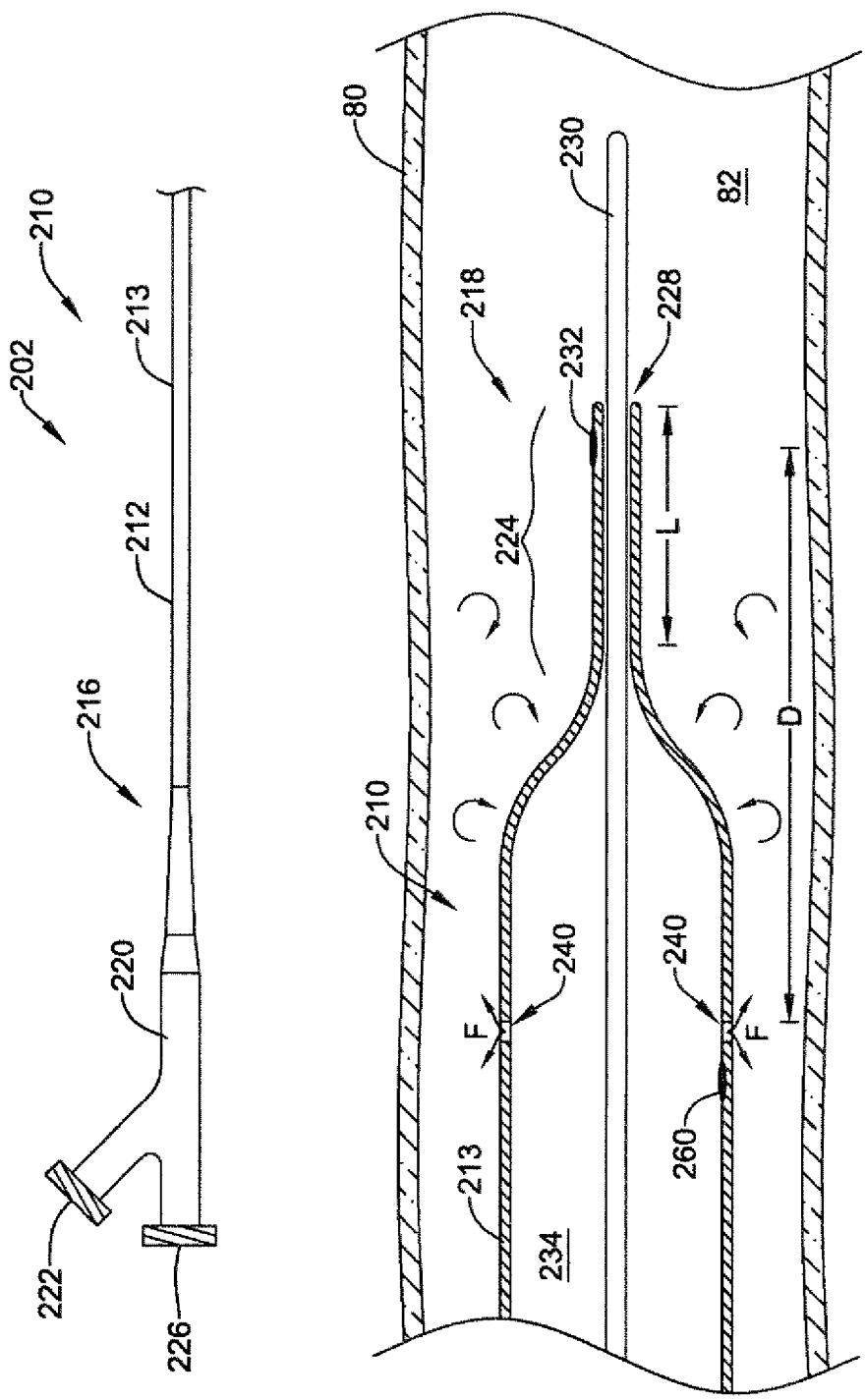
FIG. 8 is a schematic representation of another embodiment of a catheter system for determining blood flow through a body vessel using a thermodilution technique.

Another embodiment of a catheter system 202 for determining blood flow through a body vessel using a thermodilution technique is illustrated in FIG. 8. The catheter system 202 may include an infusion catheter 210, and in some instances an associated guidewire 30. The infusion catheter 210 may include an elongate catheter shaft 212 extending distally from a hub assembly 220. The catheter shaft 212 may have a proximal end 216 attached to the hub assembly 220 and a distal end 218 opposite the proximal end 216. The catheter shaft 212 may be a single lumen catheter shaft formed of a tubular member 213 having an infusion fluid lumen 234 defined therein.

The catheter shaft 212 may include a reduced diameter distal end region 224 extending to the distal end 218 of the catheter shaft 212. A guidewire 230 may extend through the infusion fluid lumen 234 of the catheter shaft 212 from a proximal guidewire port 226 located in the hub assembly 220 to a distal guidewire port 228 at the distal tip of the reduced diameter distal end region 224. The inner diameter of the reduced diameter distal end region 224 may be closely sized to the diameter of the guidewire 230 such that substantially no infusion fluid leaks out of the catheter shaft 212 through the distal guidewire port 228. The reduced diameter distal end region 224 may have a length L of about 3 centimeters to about 6 centimeters, for example.

The hub assembly 220 may also include a proximal fluid port 222 in fluid communication with the infusion fluid lumen 234. A source of infusion fluid (not shown), such as an infusion pump, syringe, etc., may be coupled to the proximal fluid port 222 to supply infusion fluid F to the infusion fluid lumen 234.

The catheter shaft 212 may include one or more fluid infusion openings 240 (e.g., holes, apertures) located at a distal end region of the catheter 210. The fluid infusion openings 240 may be in fluid communication with the infusion fluid lumen 234 and may be configured to permit infusion fluid to exit the catheter 210 from the infusion fluid lumen 234 proximate the distal end 218 of the catheter shaft 212. For example, the catheter shaft 212 may include a plurality of fluid infusion openings 240 extending through a wall of the tubular member 213 from an inner surface of the tubular member 213 to an outer surface of the tubular member 213. The infusion openings 240 may be of a similar construction and arrangement as the infusion openings 40 of the catheter 10 described above.

The fluid infusion openings 240 may be configured to expel an infusion fluid in a radially outward direction from each of the fluid infusion openings 240 to facilitate mixing of the infusion fluid with blood flowing through the vessel lumen. In other embodiments, the fluid infusion openings 240 may be arranged in a different orientation, such as in a fashion to permit infusion fluid to be expelled generally distally from the catheter shaft 212, if desired.

The infusion catheter 210 may include a first temperature sensor 260, such as a thermistor or a thermocouple, positioned within the infusion fluid lumen 234 of the catheter shaft 212 proximate the fluid infusion openings 240. The temperature sensor 260 may be configured to be in direct contact with the infusion fluid F within the infusion fluid lumen 234 to measure the temperature $T_f$ of the infusion fluid F exiting the infusion fluid lumen 234 through the fluid infusion openings 240.

The infusion catheter 210 may also include a second temperature sensor 232, such as a thermistor or a thermocouple, positioned on an exterior of the elongated reduced diameter distal end region 224 proximate the distal end 218 of the catheter shaft 212. The second temperature sensor 232 may be positioned a distance D distal of the one or more fluid infusion openings 240. The second temperature sensor 232, mounted on the exterior of the catheter shaft 212, may be used to measure the temperature $T_b$ of the blood flowing in the lumen 82 of the blood vessel 80, as well as the temperature $T_m$ of the mixture of blood and infusion fluid flowing distal of the infusion fluid openings 240. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 232. For example, the temperature sensor 232 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 240 on the catheter shaft 212.

The measured temperatures obtained with the infusion catheter 210 may then be used to calculate the actual, absolute blood flow rate of blood in the blood vessel 80 at the target location, as well as other calculated parameters, which may be useful for the diagnosis and understanding of a number of pathophysiological conditions.

Figure 9:
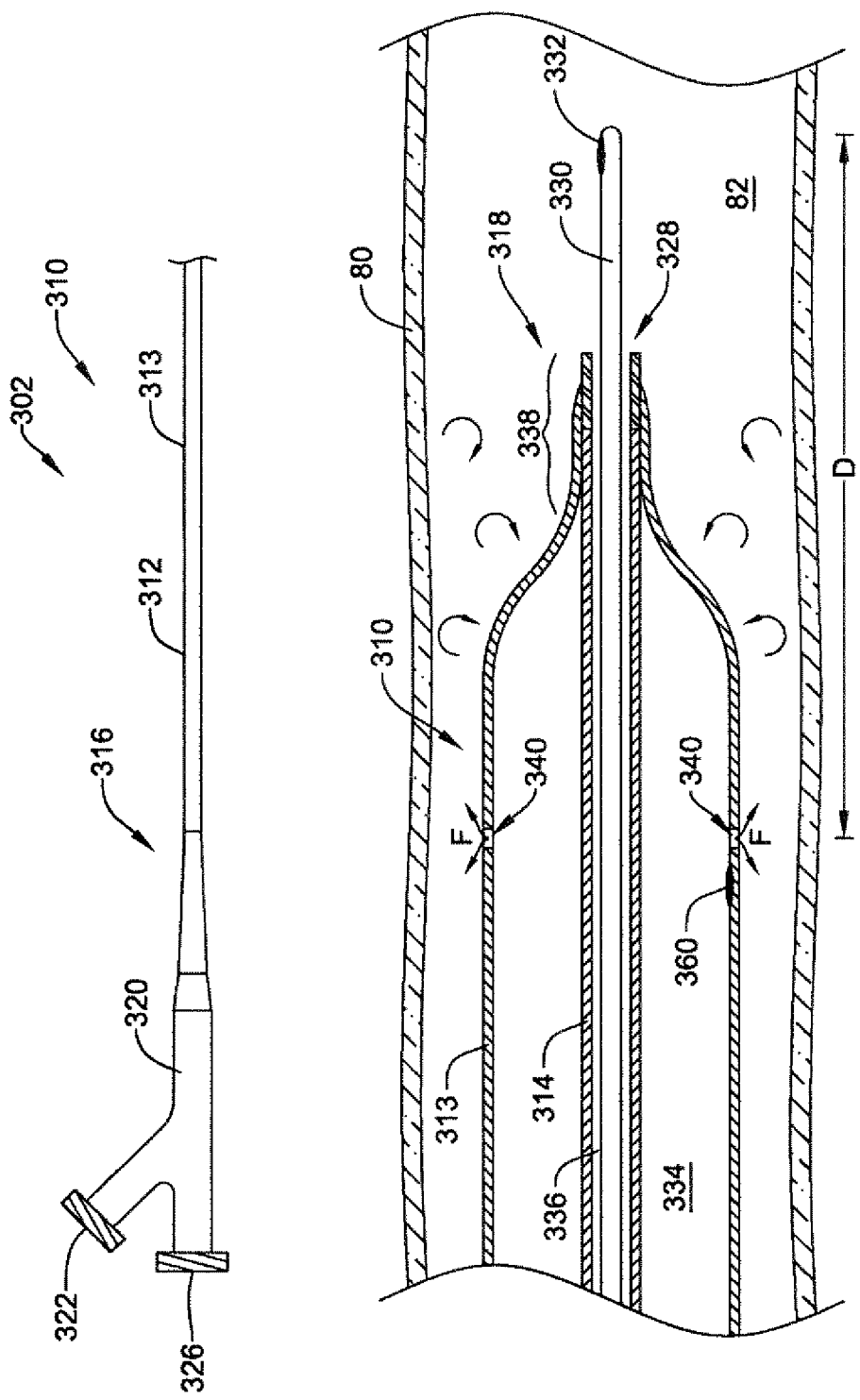
FIG. 9 is a schematic representation of another embodiment of a catheter system for determining blood flow through a body vessel using a thermodilution technique.

Another embodiment of a catheter system 302 for determining blood flow through a body vessel using a thermodilution technique is illustrated in FIG. 9. The catheter system 302 may include an infusion catheter 310, and in some instances an associated guidewire 330. The infusion catheter 310 may include an elongate catheter shaft 312 extending distally from a hub assembly 320. The catheter shaft 312 may have a proximal end 316 attached to the hub assembly 320 and a distal end 318 opposite the proximal end 316. The catheter shaft 312 may be a dual lumen catheter shaft having an infusion fluid lumen 334 and a guidewire lumen 336 extending through the catheter shaft 212 configured for advancing the infusion catheter 310 over a guidewire 330. As shown in FIG. 9, the catheter 310 may be an over-the-wire (OTW) catheter in which the guidewire lumen 336 may extend through the entire length of the catheter shaft 312 from a proximal guidewire port 326 located in the hub assembly 320 to a distal guidewire port 328 at the distal end 218 of the catheter shaft 312. However, in other embodiments, the catheter 310 may be a single-operator-exchange (SDE) catheter in which the guidewire lumen 336 extends only through a distal portion of the catheter shaft 312.

The catheter shaft 312 may include an outer tubular member 313 and an inner tubular member 314 extending through the lumen of the outer tubular member 313. In some instances, the outer tubular member 313 may coaxially surround the inner tubular member 314. The lumen of the inner tubular member 314 may define the guidewire lumen 336. The infusion fluid lumen 334 may be defined between an outer surface of the inner tubular member 314 and an inner surface of the outer tubular member 313. The hub assembly 320 may include a proximal port 322 in fluid communication with the infusion fluid lumen 334. A source of infusion fluid (not shown), such as an infusion pump, syringe, etc., may be coupled to the proximal port 322 to supply infusion fluid to the infusion fluid lumen 334.

A distal end portion 338 of the outer tubular member 313 may be a reduced diameter portion or necked portion, secured to the inner tubular member 314 to seal the infusion fluid lumen 334 proximate the distal end 318 of the catheter shaft 312. For example, the distal end portion 338 may include a tapered region in which the outer tubular member 313 tapers down to a reduced inner and/or outer diameter at the distal end of the outer tubular member 313. Thus, the inner surface of a distal end portion of the outer tubular member 313 may be secured to the outer surface of a distal end portion of the inner tubular member 314 in the distal end portion 38. The outer tubular member 313 may be secured to the inner tubular member 314, for example, by laser welding, hot jaws, or other thermal bonding method, an adhesive bonding method, or other bonding method if desired.

In some instances, the catheter shaft 312 may include a distal tip, formed as a separate component and secured at the distal end 318 of the catheter shaft 312, or the distal tip may be formed as a unitary portion of the inner tubular member 314 and/or the outer tubular member 313.

The catheter shaft 312 may include one or more fluid infusion openings 340 (e.g., holes, apertures) located at a distal end region of the catheter 310. The fluid infusion openings 340 may be in fluid communication with the infusion fluid lumen 334 and may be configured to permit infusion fluid to exit the catheter 310 from the infusion fluid lumen 334 proximate the distal end 318 of the catheter shaft 312. For example, the catheter shaft 312 may include a plurality of fluid infusion openings 340 extending through a wall of the outer tubular member 313 from an inner surface of the outer tubular member 313 to an outer surface of the outer tubular member 313. The infusion fluid openings 340 may be of a similar construction and arrangement as the infusion openings 40 of the catheter 10 described above.

The fluid infusion openings 340 may be configured to expel an infusion fluid F in a radially outward direction from each of the fluid infusion openings 340 to facilitate mixing of the infusion fluid F with blood flowing through the vessel lumen. In other embodiments, the fluid infusion openings 340 may be arranged in a different orientation, such as in a fashion to permit infusion fluid to be expelled generally distally from the catheter shaft 312, if desired.

The infusion catheter 310 may include a temperature sensor 360, such as a thermistor or a thermocouple, positioned within the infusion fluid lumen 334 of the catheter shaft 312 proximate the fluid infusion openings 340. For example, the temperature sensor 360 may be secured to the inner surface of the outer tubular member 313 proximate one of the fluid infusion openings 340. The temperature sensor 360 may be configured to be in direct contact with the infusion fluid F within the infusion fluid lumen 334 to measure the temperature $T_f$ of the infusion fluid F exiting the infusion fluid lumen 334 through the fluid infusion openings 340.

The catheter system 302 may also include a guidewire 330 sized and configured to be disposed through the guidewire lumen 336 of the infusion catheter 310 such that the infusion catheter 310 may be advanced along the guidewire 330 to a target location in the vasculature. The guidewire 330 may include a temperature sensor 332, such as a thermistor or a thermocouple, mounted on a distal end region of the guidewire 330. One illustrative embodiment of a guidewire 330 having a temperature sensor 332 mounted thereon is described in U.S. Pat. No. 6,343,514, which is incorporated by reference herein. In some instances, the guidewire 330 may also include a pressure sensor located at the distal end region of the guidewire 330 for measuring blood pressure at a target location within the vasculature. The temperature sensor 332, mounted on the guidewire 330, may be used to measure the temperature $T_b$ of the blood flowing in the lumen 82 of the blood vessel 80, as well as the temperature $T_m$ of the mixture of blood and infusion fluid flowing distal of the infusion fluid openings 340. The temperature sensor 332 may be positioned a distance D distal of the infusion fluid openings 340 when taking temperature measurements of the mixture of blood and infusion fluid. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 332. For example, the temperature sensor 332 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 340 on the catheter shaft 312.

The measured temperatures obtained with the infusion catheter 310 and the guidewire 330 may then be used to calculate the actual, absolute blood flow rate of blood in the blood vessel 80 at the target location, as well as other calculated parameters, which may be useful for the diagnosis and understanding of a number of pathophysiological conditions.

Figure 10:
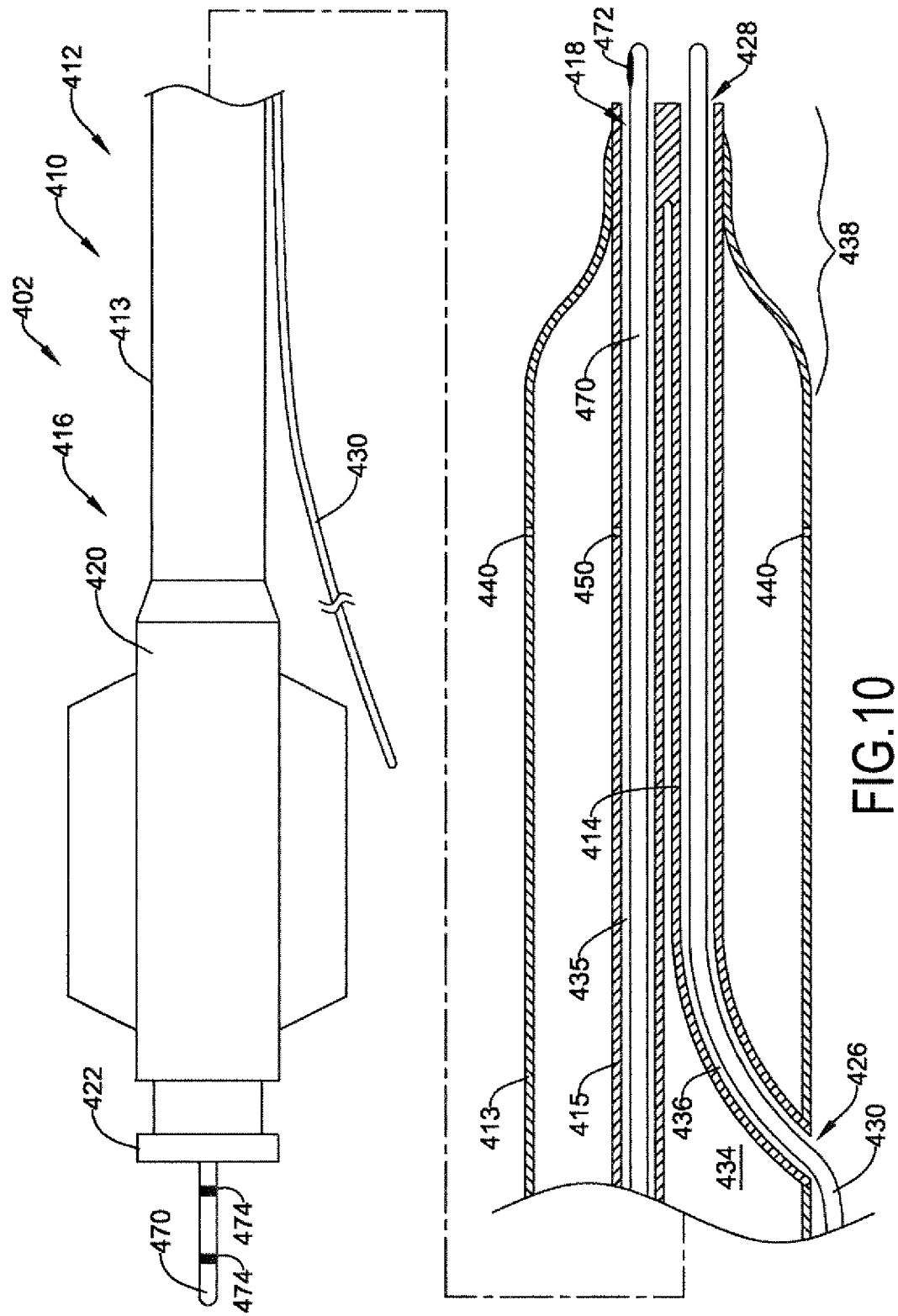
FIG. 10 is a schematic representation of another embodiment of a catheter system for determining blood flow through a body vessel using a thermodilution technique.
Figure 11A:
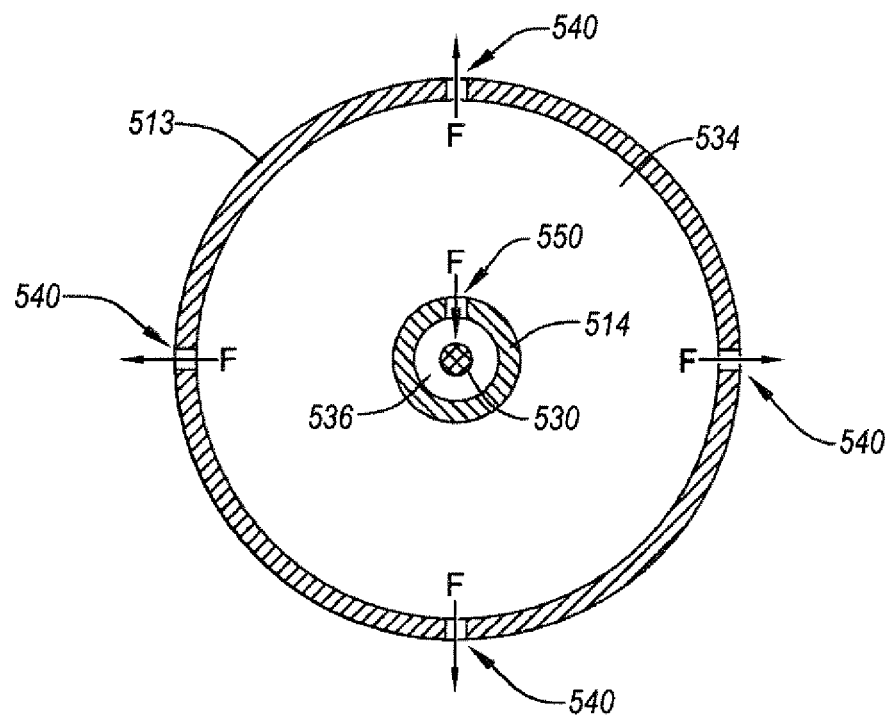
FIG. 11A is a cross-sectional view taken along line 1A-1A of FIG. 1, showing a set of 4 fluid exit openings circumferentially equidistantly arranged.
Figure 12:
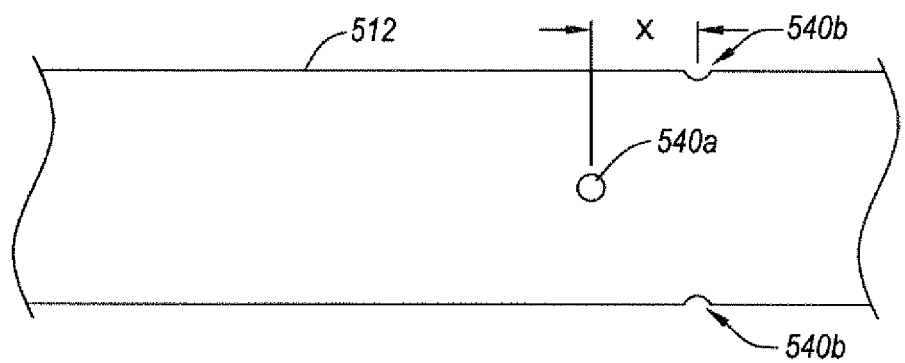
FIG. 12 is a side view of a portion of the catheter of FIG. 11 according to a variant feature with 4 fluid exit openings in quincunx.

Another embodiment of a catheter system 402 for determining blood flow through a body vessel using a thermodilution technique is illustrated in FIG. 10. The catheter system 402 may include an infusion catheter 410, and in some instances an associated temperature probe 470 and/or guidewire 430. In many respects the infusion catheter 410 may be similar to the infusion catheter 10 illustrated in FIG. 1. For example, the infusion catheter 410 may include an elongate catheter shaft 412 extending distally from a hub assembly 420, having a proximal end 416 attached to the hub assembly 420 and a distal end 418 opposite the proximal end 416. The catheter shaft 412 may be a triple lumen catheter shaft having a first, infusion fluid lumen 434 and a second, an auxiliary lumen 435 (e.g., a temperature probe lumen), and a third, guidewire lumen 436 extending along at least a portion of the catheter shaft 412 configured for advancing the infusion catheter 410 over the guidewire 430.

The catheter shaft 412 may include an outer tubular member 413 and first and second inner tubular members 415, 414 extending through the lumen of the outer tubular member 413. The infusion fluid lumen 434 may be defined by the portion of the lumen of the outer tubular member 413 exterior of the first and second inner tubular members 415, 414. The hub assembly 420 may include a proximal port 422 in fluid communication with the infusion fluid lumen 434. A source of infusion fluid (not shown), such as an infusion pump, syringe, etc., may be coupled to the proximal port 422 to supply infusion fluid to the infusion fluid lumen 434. In other embodiments, the catheter shaft 412 may be an extruded tubular member including three lumens extending therethrough, for example.

The lumen of the second inner tubular member 414 may define the guidewire lumen 436 with a distal guidewire port 428 proximate the distal end of the second inner tubular member 414 and a proximal guidewire port 426 proximate the proximal end of the second inner tubular member 414. The guidewire 430 may be extendable through the guidewire lumen 436.

The lumen of the first inner tubular member 415 may define the auxiliary lumen 435 configured for longitudinally receiving an elongate member, such as a temperature probe 470 therethrough. The auxiliary lumen 435 may extend from the proximal end of the catheter 410 to the distal end of the catheter 410, with a proximal portion of the temperature probe 470 extending proximal of the auxiliary lumen 435 (e.g., proximal of the catheter 410) and a distal portion of the temperature probe 470 extending distal of the auxiliary lumen 435 (e.g., distal of the catheter 410).

A distal end portion 438 of the outer tubular member 413 may be a reduced diameter portion or necked portion, secured to the first inner tubular member 415 and/or the second inner tubular member 414 to seal the infusion lumen 434 proximate the distal end 418 of the catheter shaft 412. For example, the distal end portion 438 may include a tapered region in which the outer tubular member 413 tapers down to a reduced inner and/or outer diameter at the distal end of the outer tubular member 413. Thus, the inner surface of a distal end portion of the outer tubular member 413 may be secured to the outer surface of a distal end portion of the first inner tubular member 415 and/or the outer surface of a distal end portion of the second inner tubular member 414 in the distal end portion 438. The outer tubular member 413 may be secured to the inner tubular members 414, 415, for example, by laser welding, hot jaws, or other thermal bonding method, an adhesive bonding method, or other bonding method if desired.

The catheter shaft 412 may include one or more fluid infusion openings 440 (e.g., holes, apertures) located at a distal end region of the catheter 410. The fluid infusion openings 440 may be in fluid communication with the infusion fluid lumen 434 and may be configured to permit infusion fluid to exit the catheter 410 from the infusion fluid lumen 434 proximate the distal end 418 of the catheter shaft 412. For example, the catheter shaft 412 may include a plurality of fluid infusion openings 440 extending through a wall of the outer tubular member 413 from an inner surface of the outer tubular member 413 to an outer surface of the outer tubular member 413. The infusion fluid openings 440 may be of a similar construction and arrangement as the infusion openings 40 of the catheter 10 described above.

The fluid infusion openings 440 may be configured to expel an infusion fluid F in a radially outward direction from each of the fluid infusion openings 440 to facilitate mixing of the infusion fluid F with blood flowing through the vessel lumen. In other embodiments, the fluid infusion openings 440 may be arranged in a different orientation, such as in a fashion to permit infusion fluid to be expelled generally distally from the catheter shaft 412, if desired.

The catheter shaft 412 may also include one or more fluid holes 450 (e.g., openings, apertures) located at the distal end region of the catheter 410. The fluid hole(s) may be in fluid communication with the infusion fluid lumen 434 and may be configured to permit infusion fluid to pass from the infusion fluid lumen 434 into the auxiliary lumen 435. For example, the catheter shaft 412 may include one or more fluid holes 450 extending through a wall of the first inner tubular member 415 from an outer surface of the first inner tubular member 415 to an inner surface of the first inner tubular member 415. The catheter shaft 412 may include one fluid hole 450 extending through the wall of the first inner tubular member 415 to permit infusion fluid F to enter the auxiliary lumen 435 from the infusion fluid lumen 434, or the catheter shaft 412 may include two, three or more such fluid holes 450, if desired.

The fluid hole(s) 450 may be a weeping hole configured to allow infusion fluid to weep or exude slowly into the auxiliary lumen 435 from the infusion fluid lumen 434. For instance, the fluid hole(s) 450 may be configured to allow infusion fluid to weep, drip, trickle, ooze or otherwise slowly exude into the auxiliary lumen 435. In some instances, the fluid hole(s) 450 may have a diameter of about 100 microns (0.100 millimeters) to about 300 microns (0.300 millimeters), about 100 microns (0.100 millimeters) to about 200 microns (0.200 millimeters), or about 200 microns (0.200 millimeters) to about 300 microns (0.300 millimeters), for example.

The catheter system 402 may also include a temperature probe 470 sized and configured to be disposed through the auxiliary lumen 435 of the infusion catheter 410. The temperature probe 470 may be longitudinally actuatable through the auxiliary lumen 435 relative to the catheter 410. The temperature probe 470 may include a temperature sensor 472, such as a thermistor or a thermocouple, mounted on a distal end region of the temperature probe 470. One illustrative embodiment of a temperature probe 470 is a fiber optic temperature sensor available from Neoptix. The temperature sensor 472, mounted on the temperature probe 470, may be used to measure the temperature $T_b$ of the blood flowing in the lumen of the blood vessel, as well as the temperature $T_m$ of the mixture of blood and infusion fluid flowing distal of the infusion fluid openings 440. The temperature sensor 472 may be positioned a distance distal of the infusion fluid openings 440 when taking temperature measurements of the mixture of blood and infusion fluid. In some instances, the distance may be about 3 centimeters or more, about 4 centimeters or more, about 5 centimeters or more, or about 6 centimeters or more to ensure the infusion fluid F completely mixes with the blood prior to reaching the temperature sensor 472. For example, the temperature sensor 472 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 440 on the catheter shaft 412.

The temperature probe 470 may be longitudinally actuated relative to the catheter 410 to position the sensor 472 inside the auxiliary lumen 435 to obtain a measurement of the temperature $T_f$ of the infusion fluid. For example, the sensor 472 may be positioned within the auxiliary lumen 435 adjacent to the fluid hole 450 extending through the first inner tubular member 415. The infusion fluid F (e.g., saline) may be delivered through the infusion fluid lumen 434 to the distal end region of the catheter 410. For example, the infusion fluid F may be provided to the distal region of the catheter 410 at a pressure of about 1 ATM to about 30 ATM. A small amount of the infusion fluid F may enter the auxiliary lumen 435 through the fluid hole(s) 450 from the infusion fluid lumen 434. Accordingly, with the temperature sensor 472 positioned in the auxiliary lumen 435, the actual temperature $T_f$ of the infusion fluid F at the distal end region of the catheter 410 may be measured and recorded. For example, the temperature sensor 472 may be positioned adjacent to the fluid hole(s) 450 such that infusion fluid F passing into the auxiliary lumen 435 may come into direct contact with the temperature sensor 472 in the auxiliary lumen 435. In other instances, the temperature sensor 472 may be otherwise positioned within the auxiliary lumen 435 such that infusion fluid F located in the auxiliary lumen 435 may come into direct contact with the temperature sensor 472 in the auxiliary lumen 435.

The temperature probe 470 may include a visual marker system including markings or indicia 474 on a proximal portion of the temperature probe 470 that medical personnel may use to determine the position of the temperature sensor 472 relative to the fluid infusion opening(s) 440 and/or the fluid hole(s) 450. The markings or indicia 474 may be located on the temperature probe 470 proximal of the hub assembly 420 for direct observation by an operator. In some instances, the temperature probe 470 may include a first mark or indicia 474 at a known location corresponding to when the temperature sensor 472 is positioned proximate the fluid hole 450, a second mark or indicia 474 at a known location corresponding to when the temperature sensor 472 is located a first known distance (e.g., 3 centimeters) distal of the catheter 410 and thus the fluid infusion openings 440, a third mark or indicia 474 at a known location corresponding to when the temperature sensor 472 is at a second distance (e.g., 4 centimeters) distal of the catheter 410 and thus the fluid infusion openings 440, a fourth mark or indicia 474 at a known location corresponding to when the temperature sensor 472 is at a third distance (e.g., 5 centimeters) distal of the catheter 410 and thus the fluid infusion openings 440, a fifth mark or indicia 474 at a known location corresponding to when the temperature sensor 472 is at a fourth distance (e.g., 6 centimeters) distal of the catheter 410 and thus the fluid infusion openings 440, etc.

The measured temperatures obtained with the temperature probe 470 may then be used to calculate the actual, absolute blood flow rate of blood in a blood vessel at the target location, as well as other calculated parameters, which may be useful for the diagnosis and understanding of a number of pathophysiological conditions.

According to a further aspect of the invention, it has been unexpectedly discovered by the inventors that the above described catheter using thermodilution for determining blood flow is capable of being also used, either with the essential same structure as described above for the embodiments of FIGS. 1 to 10, or with variant embodiment structures for instance as shown on FIGS. 11 to 20, without limitation, for performing the destruction of a body obstruction in a body lumen, in particular a body vessel of a live being. A body vessel should be understood as meaning any vessel in a live being wherein blood flows, including a vessel, an artery, a coronary, etc. A live being may be a human and an animal. An obstruction in a body or blood vessel may be any obstruction, for instance a thrombus, a thrombosis, or a blood clot, without any limitation.

Indeed, it had been unexpectedly discovered by the inventors that by choosing fluid exit opening(s) having a predetermined diameter in the range of about 50 micrometer to about 110 micrometers and in a particular variant ranging between 70 microns and 100 microns, and a predetermined fluid pressure ranging between about 20×101,325 Pa or 20 Atm and about 50×101,325 Pa, or 50 Atm, in particular ranging between at least, or more than 30×101,325 Pa or 30 Atm and about 50×101,325 Pa, or 50 Atm, the fluid flow exiting the fluid exit openings has a shearing force causing a mechanical destruction of this body obstruction, which is in general either a thrombosis, or blood clot.

The selected size of the fluid exit openings depends upon the value of the pressure of the injected fluid and the value of pressure depends also upon the number of fluid exit openings present on the outer wall of the catheter, as above said and below detailed.

According to a particular variant feature there is at least one set of 4 fluid exit openings circumferentially equidistantally arranged. This at least one set four fluid exit openings may be either located within the same plane substantially perpendicular to the vessel longitudinal axis or located in quincunx within two distinct parallel planes substantially perpendicular to the vessel longitudinal axis.

According to another particular variant feature there is at least two sets of 4 fluid exit openings circumferentially equidistantally arranged and finally according to a further particular variant feature there is at least three sets of 4 fluid exit openings circumferentially equidistantally arranged.

Figure 19:
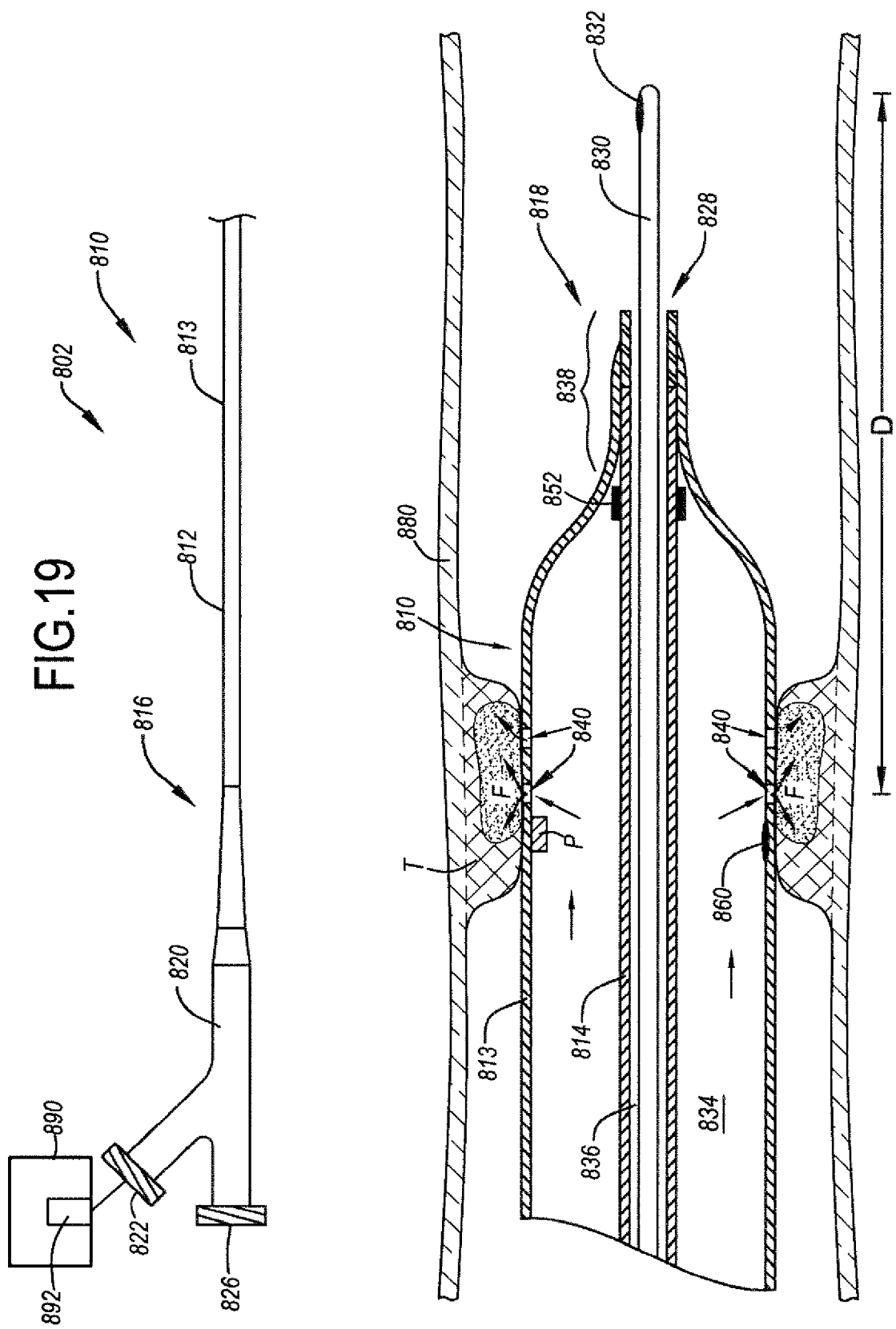
FIG. 19 is a schematic representation of another embodiment of a catheter system for performing destruction of a body obstruction, for instance a thrombus, through a body vessel of a live being, let it be a human or an animal.
Figure 20:
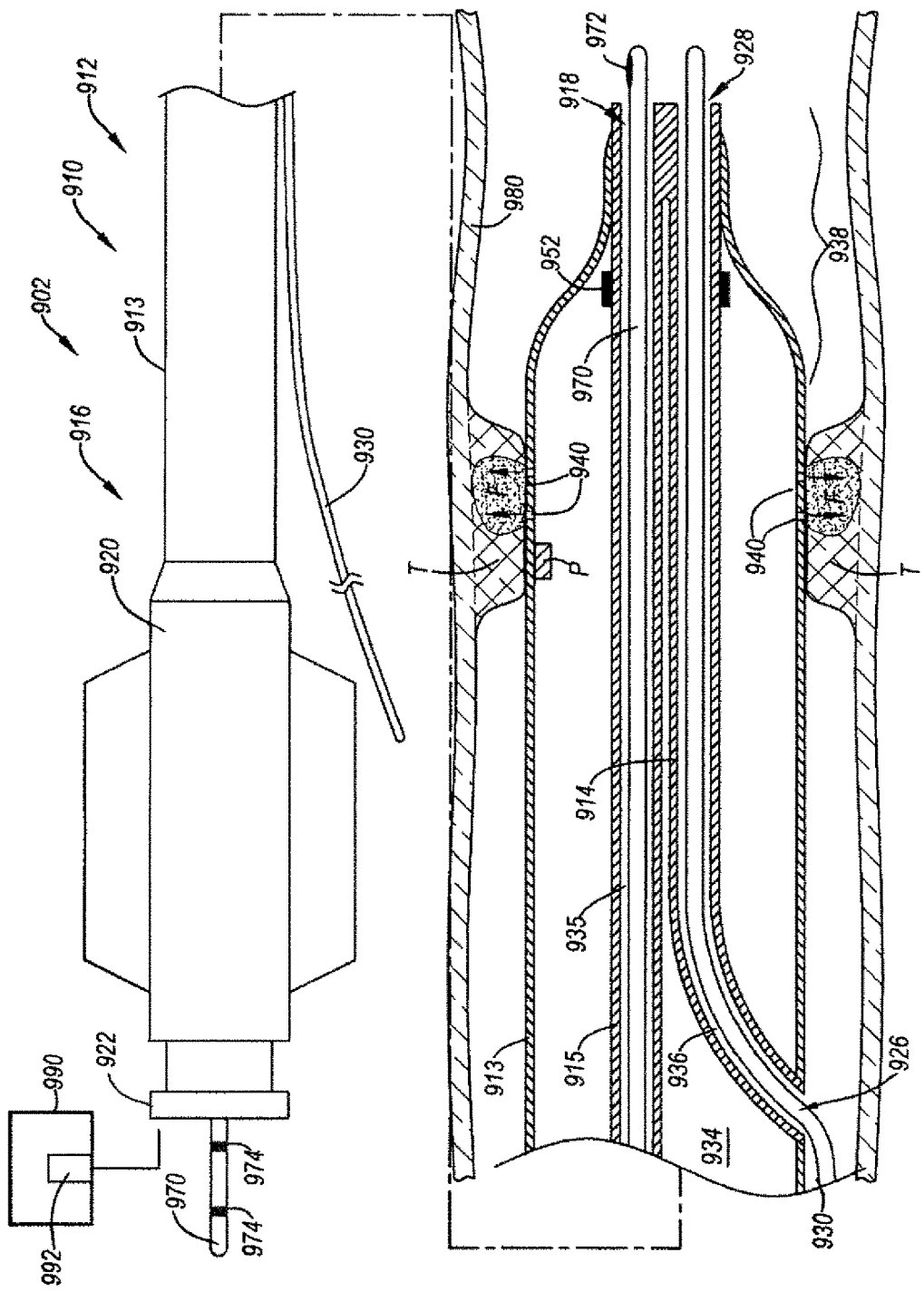
FIG. 20 is a schematic representation of another embodiment of a catheter system for performing destruction of a body obstruction, for instance a blood clot, through a body vessel of a live being, let it be a human or an animal.

Under this new use of destruction of body vessel obstruction, there is no need for communication with the central lumen for determining fluid temperature as it was required in the infusion catheter of FIGS. 1 to 10 and some embodiments of FIGS. 11 to 20, like FIGS. 18, 19 and 20 lack this communication but it may still be useful to keep on the guidewire 830 or 970 a temperature sensor like for instance shown on FIGS. 19 and 20, respectively.

Accordingly, the invention catheter system for performing destruction of a body obstruction in a body vessel is represented on FIGS. 11 to 20 similar to FIGS. 1 to 10. For this reason, the reference numbers of similar constructive elements are merely increased each time by 100 as is well understandable for one skilled in the art.

Referring now to FIG. 11, a catheter system 502 is shown similar to that of FIG. 1, comprising an elongate catheter 510 having a catheter shaft 512 extending distally from the hub assembly 520, said catheter shaft comprising a proximal end 516 attached to the hub assembly and a distal end 518 opposite the proximal end 516. The catheter shaft 512 may be a dual lumen having a first, fluid lumen 534 and a second lumen 536 for insertion of an elongate element which can be a guidewire 530 extending along at least a portion of the catheter shaft 512 configured for advancing the catheter 510 over the guidewire 530. For example, in some embodiments, the catheter 510 maybe an over the wire (OTW) catheter in which the guidewire lumen 536 may extend through the entire length of the catheter shaft 512 from the distal end 518 to the proximal end 516 as shown in FIGS. 18 and 19 further described farther.

In other embodiments, such as the embodiments shown in FIGS. 11,11A, 12 to 17 and 20, the catheter may be a single operator-exchange (SOE) in which the guidewire lumen 536 extends only through a distal portion of the catheter shaft 512 or 912.

The catheter shaft 512 may include an outer tubular member 513 and an inner tubular member 514 disposed within, and extending through, a first fluid lumen 534 of the outer tubular member 514; said first fluid lumen 534 is thus defined between the inner tubular member 514 and the outer tubular member 513 and a second lumen 536 defined by the inner tubular member 514.

With the SOE catheter construction of FIG. 11, the fluid lumen 534 may be defined between an outer surface of the inner tubular member 514 and the inner surface of the outer tubular member 513 and is understandably extending from the proximal end 516 and the distal end 518.

One or more fluid exit openings 540 are located at a distal end region of the catheter configured to permit fluid to exit the catheter from the first fluid lumen 534.

The hub assembly 520 may include a proximal port 522 in fluid communication with the fluid lumen 534. A control device 590 may include fluid pressure means 592 located external of the catheter ahead from the proximal end 516 and coupled to the proximal port 522 for delivering said fluid in the first fluid lumen 534 at a pressure range predetermined to cause destruction of said obstruction when exiting the fluid exit openings 540.

The catheter system may further comprise an elongate member 530 advanceable through the second lumen 536 of the catheter.

According to a variant, the elongate member may comprise a temperature sensor 532 positioned on a distal end portion of the elongate member 530.

According to a further variant, the temperature sensor 532 on the distal end portion of the elongate member 530 is positionable ahead of the distal end 518 of the catheter to measure temperature in the blood vessel 580 shown on FIGS. 14 to 17.

The lumen 536 of the inner tubular member 514 may define the elongate member lumen 536, here shown as a guidewire lumen 536 with a distal port 528 proximate the distal end 518, and a proximate guidewire port 526 proximate the proximal end of the inner tubular member 514.

According to a further variant embodiment, the one or more fluid exit openings 540 extend through a wall of the outer tubular member 513 from an inner surface of the outer tubular member to an outer surface of the outer tubular member.

According to a further variant, embodiment, the one or more fluid exit openings 540 are configured to generate a jet of fluid exiting the catheter, in particular radially substantially perpendicularly to the surface of the outer tubular member 513, and at a pressure sufficient to cause mechanical destruction of the body obstruction like a thrombosis T shown on FIGS. 15-20.

In a particular variant embodiment, the one or more fluid exit openings 540 include at least one set of four fluid exit openings 540 equidistantly spaced circumferentially around the outer tubular member as shown on FIGS. 11, 11A, 16 and 18. In this embodiment of FIGS. 11, 11a, the 4 fluid exit openings are located in the same plane substantially perpendicular to the longitudinal axis of the catheter and therefore also of the body vessel 580. In a variant embodiment shown on FIGS. 12, 15, and 17, the 4 fluid exit openings 540a and 540b, or 640a and 640b, are located in two distinct parallel planes substantially perpendicular to the longitudinal axis of the catheter and therefore also of the body vessel 580. These two parallel planes may be spaced apart of a longitudinal distance x as for FIG. 2, such as about 0.5 millimeters, about 1 millimeter, about 2 millimeters or about 3 millimeters away.

In another particular variant embodiment, the one or more fluid exit openings include at least two sets of four fluid exit openings 840 and 940 equidistantly spaced circumferentially around the outer tubular member 880 and 980 as shown on FIGS. 19 and 20, respectively.

Figure 13:
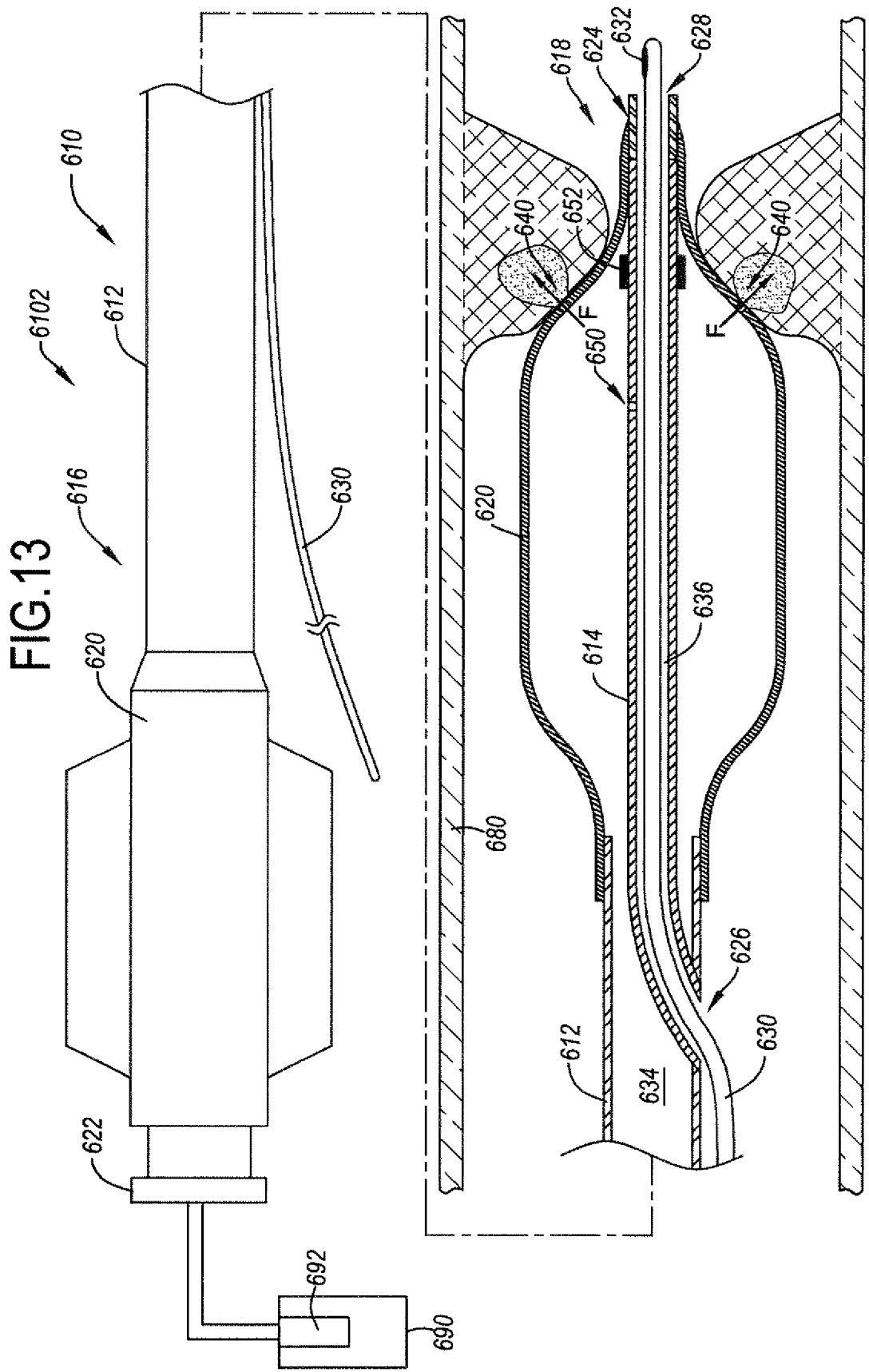
FIG. 13 is a schematic representation of an alternative embodiment of a catheter system including a catheter and associated guidewire for performing destruction of a body obstruction through a body vessel of a live being, let it be a human or an animal.

In another particular variant embodiment, one or more fluid holes 550, FIG. 11, or fluid holes 650, FIG. 13, are located at the distal end region of the catheter, and are configured to permit fluid to pass from the first fluid lumen 534 into the second lumen 536 and said one or more fluid holes 550 extend through a wall of the inner tubular member 536 from an outer surface of the inner tubular member to an inner surface of the inner tubular member.

According to a variant feature, the one or more fluid holes 550, 650 are one or more weeping holes configured to allow fluid to weep into the second lumen.

According to a variant embodiment, the one or more fluid holes 550, 650 have a diameter ranging between about 100 micrometers and about 300 micrometers.

According to a variant embodiment, the elongate catheter shaft 512 includes an elongated reduced diameter region 538 extending distal of the one or more fluid exit openings 540 to the distal end of the elongate catheter shaft 512.

According to a further variant embodiment, a first temperature sensor 760, 860, see FIGS. 18, 19, is positioned within the first fluid lumen of the catheter shaft proximate the one or more fluid exit openings 740, 840, the first temperature sensor 760, 860, configured to be in direct contact with the fluid within the lumen to measure a temperature of the fluid exiting the lumen through the one or more fluid exit openings 740, 840.

According to a further variant embodiment, the catheter may further comprise a second temperature sensor 732 positioned on an exterior of the elongated reduced diameter region 724 proximate the distal end 718 of the elongate catheter shaft 710, as shown on FIG. 18.

According to a further variant feature, the second temperature sensor 732 is positioned at least 4 centimeters distal of the one or more fluid exit openings 740.

According to a further variant embodiment, the distal end of the inner tubular member is sealingly secured to the distal end of the elongate catheter shaft.

As above said the elongate member 530 may comprise a guidewire advanceable through the inner tubular member 514.

According to a further variant embodiment, the guidewire 530 may comprise a temperature sensor 532 positioned on a distal end portion of the guidewire to measure a temperature of a blood/fluid mixture in the body lumen distal of the one or more fluid exit openings 540.

According to a further variant embodiment, the catheter may comprise at least one pressure sensor P in the vicinity of at least one fluid exit opening 540, FIG. 11 or 640, FIG. 13, or 740, FIG. 18, or 840, FIG. 19 or 940, FIG. 20.

According to a further variant embodiment, in all embodiments of FIGS. 11 to 20, the fluid is a liquid selected from a saline and an aqueous solution compatible with blood. In a variant embodiment, this saline solution may comprise at least one clot or thrombosis dissolution aid. These dissolution aids are well known to those skilled in the art.

According to a further variant embodiment, in all embodiments of FIGS. 11 to 20, the fluid exit opening(s) have a diameter ranging between about 50 microns (0.050 millimeters) and about 110 microns (0.110 millimeters). The diameter size selected is usually adapted to the pressure of the fluid and said fluid pressure at the entrance of said catheter or at the vicinity of at least one fluid exit opening ranges between about 20×101,325 Pa or 20 ATM and about 50×101,325 Pa or 50 ATM.

According to a variant embodiment, the fluid exit opening(s) have a diameter ranging between about 70 microns (0.070 millimeters) and about 100 microns (0.100 millimeters).

According to a further variant embodiment, the pressure of the fluid at the entrance of said catheter or at the vicinity of at least one fluid exit opening ranges between at least, or more than, 30×101,325 Pa or 30 ATM and 50×101,325 Pa or 50 ATM. This pressure is particularly adapted with a size of the orifices ranging between about 70 microns (0.070 millimeters) and about 100 microns (0.100 millimeters) and the pressure depends also upon the number of fluid exit openings present on the outer wall of the catheter as is well understandable for one skilled in the art.

As for the embodiments of FIGS. 1 to 10, all embodiments of FIGS. 11 to 20 may also include one or more radiopaque markers 552, FIGS. 11 and 16, or 652, FIG. 13, or 752, FIG. 18, or 852, FIG. 19 or 952, FIG. 20, for the same reasons as explained for the embodiments of FIGS. 1 to 10.

As shown on the drawings, FIG. 13 relates to a variant embodiment of a Single Operator Exchange (SOE) catheter similar to that of FIG. 11. Here, the catheter may include an outer tubular member 613 and an inner tubular member 614 disposed within, and extending through, a first fluid lumen 634 of the outer tubular member 614; said first fluid lumen 634 is thus defined between the inner tubular member 614 and the outer tubular member 613 and a second lumen 636 defined by the inner tubular member 614. Further, the catheter shaft 612 may extend distally from a hub assembly 620 itself which may include a proximal port 622 in fluid communication with the fluid lumen 634. A control device 690 may include fluid pressure means 692 which may be located external of the catheter ahead from the proximal end 616 and coupled to the proximal port 622 for delivering said fluid in the first fluid lumen 634 at a pressure range predetermined to cause destruction of said obstruction when exiting the fluid exit openings 640.

The catheter system may further comprise an elongate member 630 advanceable through the second lumen 636 of the catheter.

The catheter may include in this variant embodiment similar to that of FIG. 3, an inflatable balloon 620 mounted on a distal region of the catheter shaft 612 The balloon may include a proximal waist secured for instance thermally or adhesively bonded, to a distal end of the outer tubular member 613 and a distal waist also secured to a distal end 624 of the inner tubular member 614. In this variant embodiment, the fluid lumen 634 extending along the catheter shaft may be in fluid communication with the interior of the inflatable balloon 620 to deliver said fluid to the inflatable balloon. Here, the inflatable balloon may include one or more fluid exit openings 640 extending through a wall of the balloon 640 and configured to permit fluid to exit the balloon 620 from the fluid lumen 634. It is well understandable that the balloon 620 is inflated by the fluid pressure flowing within the fluid lumen 634. In one illustrative embodiment as shown on FIG. 13, the balloon may include at least one set of four fluid exit openings 640, equidistantly spaced circumferentially around the balloon 620. In a particular embodiment, the fluid exit openings may be located on the distal cone portion of the balloon 620 as shown on FIG. 13, or may be on a cylindrical body portion of the balloon 620 or on both, as shown on FIG. 13, the catheter may be positioned to be blocked by the cone portion of the balloon 620 against an obstruction ahead like a thrombosis T, or a clot or even a cholesterol deposit so that when the fluid is exiting under said predetermined pressure, the jet(s) of fluid will cause mechanical or physical destruction of the obstruction T.

Figure 14:
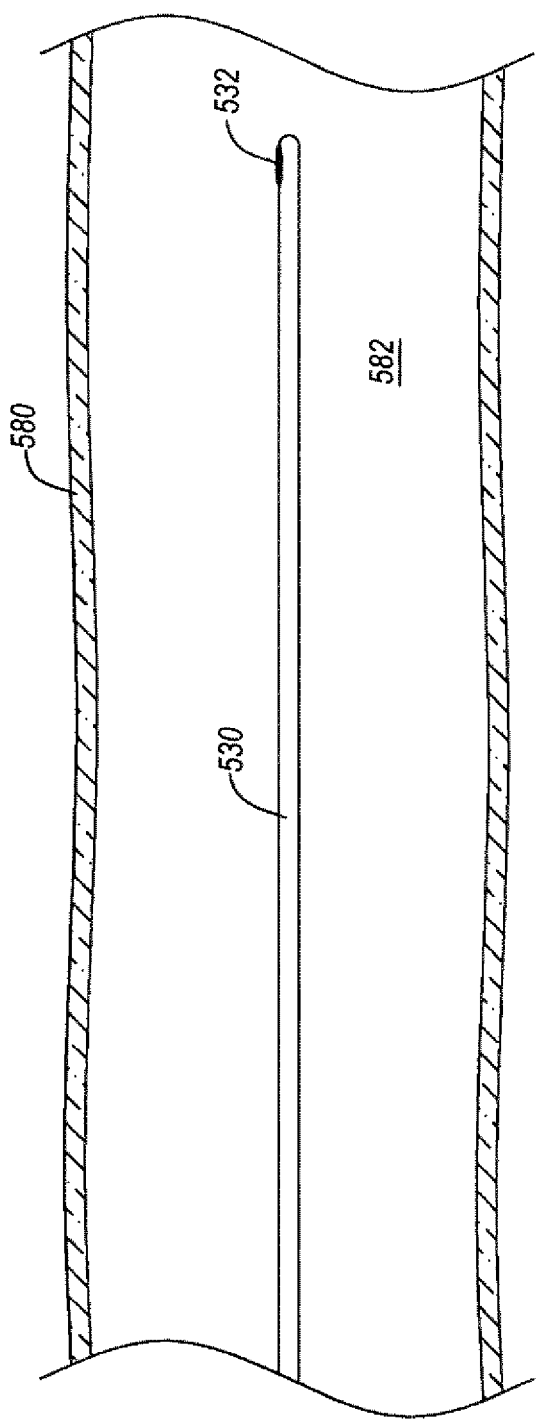
FIGS. 14-17 illustrate aspects of an exemplary method of performing destruction of a body obstruction through a body vessel using the catheter system of FIG. 11.

FIGS. 14-17 illustrate aspects of an exemplary method of destruction of an obstruction like T in a body vessel 580 using the catheter system of FIG. 11. As shown in FIG. 14, an elongate member 530 configured as a guidewire, here bearing a temperature sensor 532 mounted on a distal region thereof, may be advanced through a body lumen blood vessel 580 of a live being, for instance a human or an animal, to a desired target location T shown on FIGS. 15 to 17, namely an obstruction like a thrombosis, or blood clot, or a cholesterol deposit, for its destruction.

Figure 15:
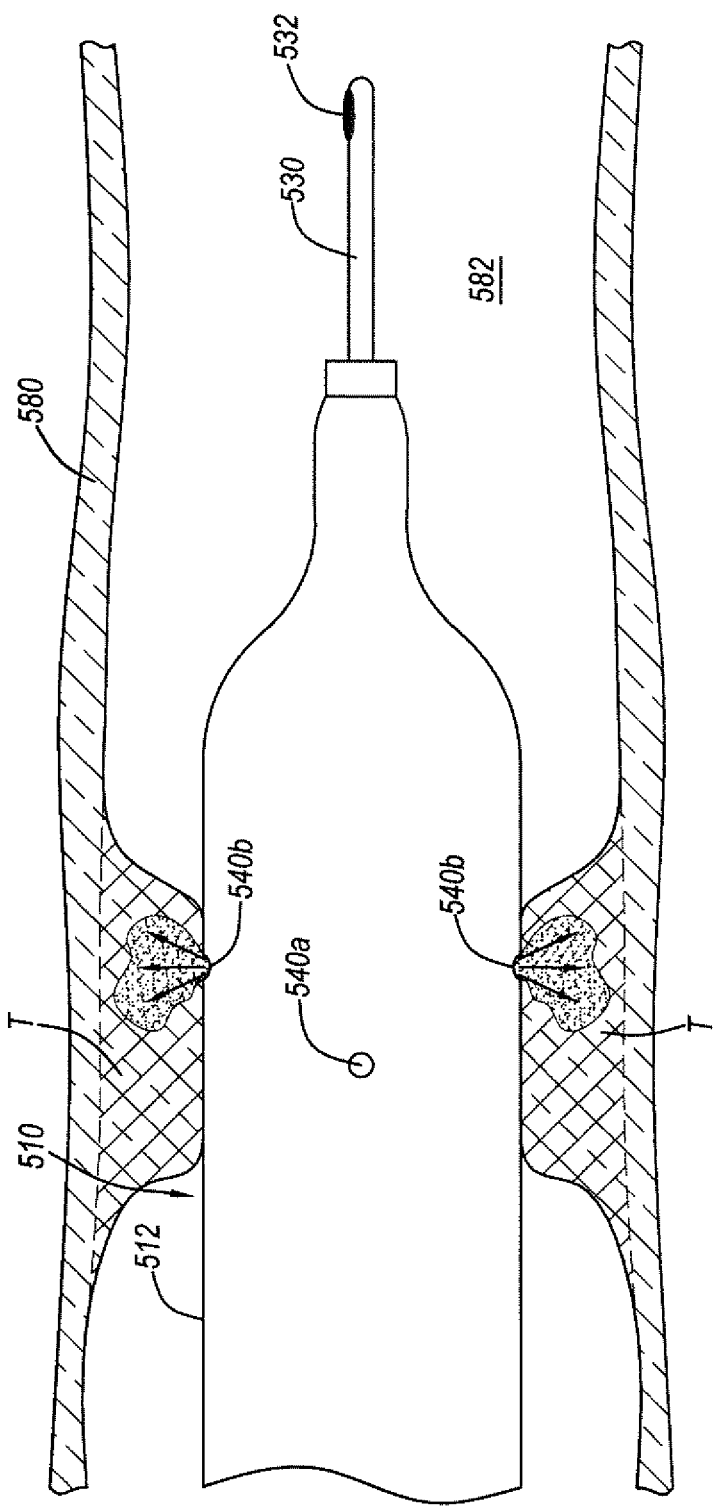
Figure 16:
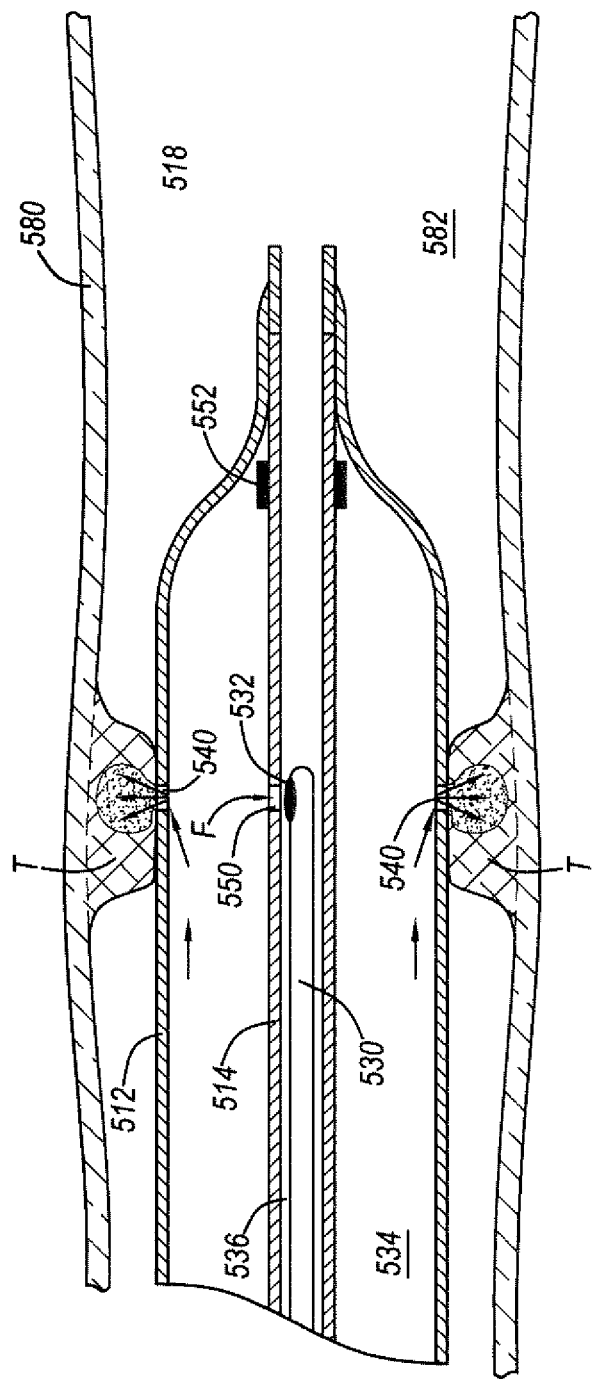
Figure 17:
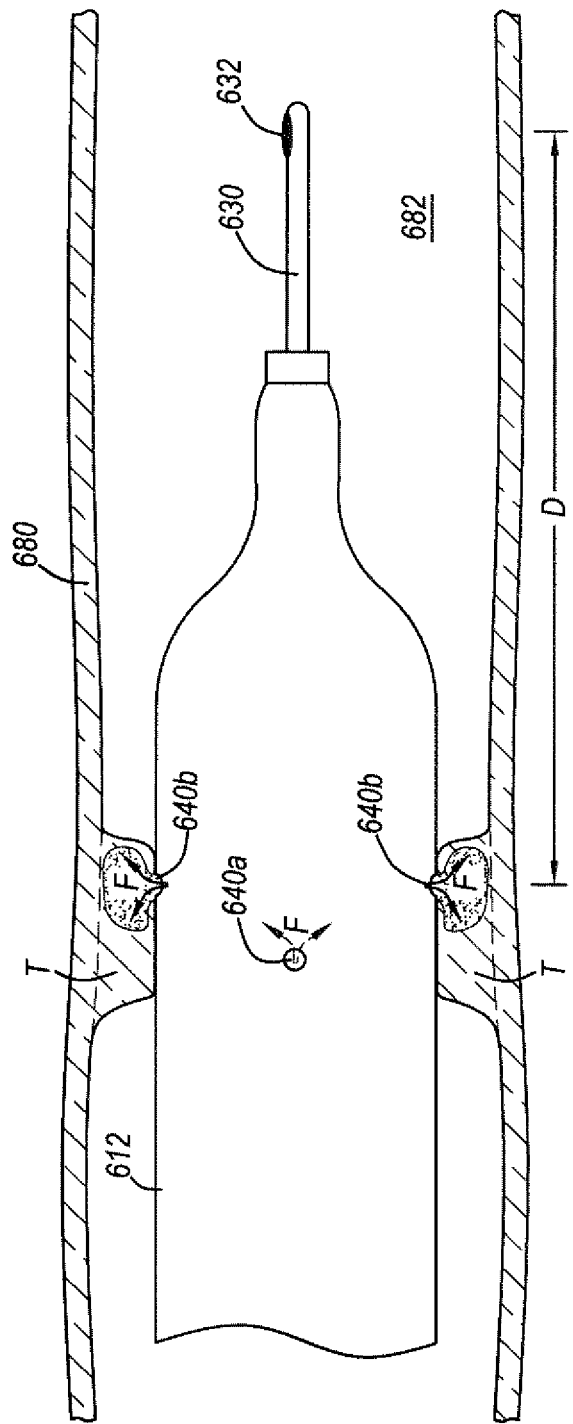

The catheter 510 may then be advanced over the guide wire 530 to the target location T as shown on FIGS. 15 to 17. Alternatively, the catheter 510 may be advanced on a conventional guidewire to the target location and then the guidewire 530 with the temperature sensor 532 may replace it when it is desired to take temperature in the blood vessel. When desired, the guidewire 530 may be withdrawn proximally to reposition the temperature sensor adjacent the fluid hole 550 as shown on FIG. 16 to measure temperature of the fluid in the vicinity of the exit openings 540. Further the temperature sensor 532 on the guidewire 530 may be advanced to a location distal of the catheter as shown on FIG. 17, for instance at a distance D from the fluid exit openings 540. This distance D may range between 3 and 6 centimeters or more to measure and check temperature in the blood vessel 580.

Thus, according to a variant embodiment, the temperature of the fluid injected under pressure from pressure means 592 is set at a desired value which may be useful for the destruction of the obstruction T while being compatible with the blood. This fluid temperature may range between about 20, or room temperature, and about 35° C.

The fluid flow rate of the fluid F may be set to any desired flow rate which in combination with the fluid pressure will result in a quick destruction of the obstruction T. This fluid flow rate may range between about 15 ml/min and about 50 ml/min.

The pressure means usually may be a pressure fluid, in particular liquid, pump.

Another catheter embodiment is shown on FIG. 18, which is an Over The Wire (OTW) catheter and similarly comprises a catheter system 702 similar to that of FIG. 8, comprising an elongate catheter 710 having a catheter shaft 712 extending distally from the hub assembly 720, said catheter shaft comprising a proximal end 716 attached to the hub assembly 720 and a distal end 718 opposite the proximal end 716. The catheter shaft 712 may be also a double lumen having a first outer fluid lumen 734, and a second inner lumen 714 defined therein. The catheter shaft 712 may include a reduced diameter distal end region 724 extending to the distal end 718 of the catheter shaft to help in sliding the catheter, the inner lumen 714 as for the other OTW embodiments is serving as a sliding guide for the elongate element 730 which may be configured as a guide wire. Thus, the inner diameter of the inner lumen 714 may be closely sized to the diameter of the guide wire 730 such that guiding and sliding of the guide wire is proper. Since the catheter 710 is here an over the wire (OTW) catheter, the guidewire lumen 736 may extend through the entire length of the catheter shaft 712 from the distal end 718 to the proximal end 716. The Hub assembly 720 has a specific fluid entrance 722 linked to a control device 790 comprising fluid pressure means 792 for injection of fluid under pressure into the fluid lumen 734, which will exit through the fluid exit openings 740 to permit destruction of the obstruction T.

There may be present a pressure sensor P in the vicinity of a fluid exit opening 840.

Another embodiment of a catheter system is shown on FIG. 19 and the catheter system is now referenced 802 similar to that of FIG. 9, comprising an elongate catheter 810 having a catheter shaft 812 extending distally from the hub assembly 820, said catheter shaft comprising a proximal end 816 attached to the hub assembly and a distal end 818 opposite the proximal end 816. The catheter shaft 812 may be a dual lumen having a first, outer fluid lumen 834 and a second inner lumen 836 for insertion of an elongate element which can be a guidewire 830 extending along at least a portion of the catheter shaft 812 configured for advancing the catheter 580 over the guidewire 830. Again and in that embodiment, the catheter 810 is an over the wire (OTW) catheter in which the guidewire lumen 836 may extend through the entire length of the catheter shaft 812 from the distal end 818 to the proximal end 816.

Also, the hub assembly 820 has a specific fluid entrance 822 linked to a control device 890 comprising fluid pressure means 892 for injection of fluid under pressure into the fluid lumen 834, which will exit through the fluid exit openings 840.

There may also be present a pressure sensor P in the vicinity of a fluid exit opening 840 to measure pressure in the vicinity of the fluid exit opening 840.

As shown on the drawings, FIG. 20 relates to a further variant embodiment of a Single Operator Exchange (SOE) catheter similar to that of FIG. 11 and FIG. 13. The catheter system 902 may include an elongate catheter 910, and in some instances an associated temperature probe 970 and/or guidewire 930. In many respects the catheter 910 may be similar to the infusion catheter 10 illustrated in FIG. 1. For example, the infusion catheter 910 may include an elongate catheter shaft 912 extending distally from a hub assembly 920, having a proximal end 916 attached to the hub assembly 920 and a distal end 918 opposite the proximal end 916. The catheter shaft 912 may be a triple lumen catheter shaft having a first fluid lumen 934 and a second, an auxiliary lumen 935 (e.g., a temperature probe lumen), and a third, guidewire lumen 936 extending along at least a portion of the catheter shaft 912 configured for advancing the infusion catheter 910 over the guidewire 930.

The catheter shaft 912 may include an outer tubular member 913 and first and second inner tubular members 915, 914 extending through the lumen of the outer tubular member 913. The fluid lumen 934 may be defined by the portion of the lumen of the outer tubular member 913 exterior of the first and second inner tubular members 915, 914. The hub assembly 920 may include a proximal port 922 in fluid communication with the fluid lumen 934. A source of infusion fluid, such as an infusion fluid, in particular liquid pump, syringe, etc., may be coupled to a pressure means 992 included in a command central 990 and coupled to the proximal port 922 to supply fluid to the fluid lumen 934 and then to the fluid exit openings 940. In other embodiments, the catheter shaft 912 may be an extruded tubular member including three lumens extending therethrough, for example.

The lumen of the second inner tubular member 914 may define the guidewire lumen 936 with a distal guidewire port 928 proximate the distal end of the second inner tubular member 914 and a proximal guidewire port 926 proximate the proximal end of the second inner tubular member 914. The guidewire 930 may be extendable through the guidewire lumen 936.

The lumen of the first inner tubular member 915 may define the auxiliary lumen 935 configured for longitudinally receiving an elongate member, such as a temperature probe 970 therethrough. The auxiliary lumen 935 may extend from the proximal end of the catheter 910 to the distal end of the catheter 910, with a proximal portion of the temperature probe 970 extending proximal of the auxiliary lumen 935 (e.g., proximal of the catheter 910) and a distal portion of the temperature probe 970 extending distal of the auxiliary lumen 935 (e.g., distal of the catheter 910).

A distal end portion 938 of the outer tubular member 913 may be a reduced diameter portion or necked portion, secured to the first inner tubular member 915 and/or the second inner tubular member 914 to seal the fluid lumen 934 proximate the distal end 918 of the catheter shaft 912. For example, the distal end portion 938 may include a tapered region in which the outer tubular member 913 tapers down to a reduced inner and/or outer diameter at the distal end of the outer tubular member 913. Thus, the inner surface of a distal end portion of the outer tubular member 913 may be secured to the outer surface of a distal end portion of the first inner tubular member 915 and/or the outer surface of a distal end portion of the second inner tubular member 914 in the distal end portion 938. The outer tubular member 913 may be secured to the inner tubular members 914, 915, for example, by laser welding, hot jaws, or other thermal bonding method, an adhesive bonding method, or other bonding method if desired.

The catheter shaft 912 may include one or more fluid exit openings 940 (e.g., holes, apertures) located at a distal end region of the catheter 910. The fluid exit openings 940 may be in fluid communication with the fluid lumen 934 and may be configured to permit infusion fluid to exit the catheter 910 from the infusion fluid lumen 934 proximate the distal end 918 of the catheter shaft 912. For example, the catheter shaft 912 may include a plurality of fluid exit openings 940 extending through a wall of the outer tubular member 913 from an inner surface of the outer tubular member 413 to an outer surface of the outer tubular member 413. The fluid exit openings 940 may be of a similar construction and arrangement as the exit openings 450 of the catheter 510 described above.

The fluid exit openings 940 may be configured to expel a fluid F in a radially outward direction from each of the fluid exit openings 940 to cause fluid F mechanically or physically destroy the obstruction T present within the vessel 980. In other embodiments, the fluid exit openings 940 may be arranged in a different orientation, such as in a fashion to permit fluid to be expelled under a pressure sufficient to cause mechanical or physical destruction of the obstruction T, if desired. On FIGS. 13, 15, to 20 it has been visualized the formation of cavities to symbolize the start of the mechanical destruction of the obstruction T. The total destruction occurs by moving several times the catheter back and forth along the length of the obstruction T as also said in the protocol mentioned farther.

In all embodiments, the catheter, as well known to one skill in the art, may be made of a flexible material compatible with blood vessels, for instance from polyether, Pebax, HDPE, polyamide, polycarbonate without limitation. It is easy to make the fluid exit openings by micro-pulsation/ablation with for instance a laser. These exit holes may be made at a distance from 7 to 8 mm of the catheter distal tip.

It is apparent that the catheter systems of FIGS. 11 to 20 are enabling to implement the invention method as follows:

The inventive method of performing destruction of a body obstruction in a body vessel of a live being, comprises:
  advancing a catheter to a desired location comprising said obstruction within the body vessel, the catheter including a catheter shaft comprising a proximal end and a distal end, comprising an outer tubular member and at least one inner tubular member disposed within the outer tubular member; a first fluid lumen defined between the inner tubular member and the outer tubular member and a second lumen defined by the inner tubular member; one or more fluid exit openings located at a distal end region of the catheter configured to permit fluid to exit the catheter from the first fluid lumen; and
  providing a delivery of a fluid through the first fluid lumen to a distal end region of the catheter and at a pressure range predetermined to exit said fluid at a pressure and for a period of time causing destruction of said obstruction.

Some variants of the methods are resulting from variant embodiments of the catheter structure.

According to a particular variant, the advancing step of said catheter within said body step comprises using an elongate member which may be configured as a guidewire.

According to another particular variant, said catheter is provided with a temperature probe, said method comprising measuring with said temperature sensor the temperature of the fluid exiting the catheter or of the blood ahead of the distal end of the catheter.

According to another particular variant, said method further comprises:
  providing at least one temperature sensor on the distal end of the elongate member and positioning the elongate member to a location distal of the catheter for measuring the temperature of the mixture of the fluid and the blood distal of the catheter.

According to a further particular variant, the catheter includes one or more fluid holes located at the distal end region of the catheter in the vicinity of at least one said fluid exit opening, the one or more fluid holes configured on the inner tube to permit the fluid to pass from the first fluid lumen into the second lumen; and repositioning the elongate member to a location in front of one said fluid hole to measure the temperature of the fluid in the vicinity of the fluid exiting the catheter.

According to a particular method variant, said method further comprises providing said fluid exit opening(s) with a diameter ranging between about 50 microns (0.050 millimeters) and about 110 microns (0.110 millimeters), and in particular between 70 microns (0.070 millimeters) and about 100 microns (0.100 millimeters). The fluid pressure at the entrance of said catheter or at the vicinity of at least one fluid exit opening ranges between about 20×101325 Pa or 20 ATM and about 50×101,325 Pa or 50 ATM, and in particular between at least, or more than, 30×101,325 Pa or 30 ATM and about 50×101,325 Pa or 50 ATM.

According to a particular variant, the catheter comprises at least one pressure sensor in the vicinity of at least one fluid exit opening and said method comprises measuring the pressure of the fluid in the vicinity of said fluid exit opening and correcting the pressure value of the fluid injected in the fluid lumen.

According to a further particular variant, said method further comprises providing said fluid as a liquid selected from a saline and an aqueous solution compatible with blood comprising at least one clot or thrombosis dissolution aid.

Herebelow is set forth a clinical protocol of thrombus fragmentation by the invention catheter as described in any of FIGS. 11 to 20, during primary Percutaneous Coronary Intervention or PCI.

Background

Thrombus is almost uniformly involved in the abrupt coronary occlusion that is responsible for an acute myocardial infarction (AMI).

Invention Goal

It is the goal of the invention that thrombus fragmentation occurs by spraying a saline liquid solution perpendicular to the longitudinal axis of the artery to prevent a large thrombus embolization during balloon inflation and stent implantation.

In addition, saline infusion has been shown to induce maximal and steady state microvascular vasodilation that might further contribute to the preservation of microvascular function in the setting of AMI.

Protocol

Patients are admitted with an ST elevation myocardial infarction or STEMI and in whom the angiogram shows a TIMI0 or TIMI1 flow in the culprit artery. TIMI 0 and TIMI 1 are scores of permeability of a coronary artery: TIMI 0=totally occluded; TIMI1=discrete opacification of the artery distal to the lesion.

The occluded segment must be located in an artery of at least 3 mm in diameter.

After angiographic documentation of a total or subtotal obstruction of the coronary artery, a regular guide wire is advanced across the thrombotic occlusion. This maneuver usually induces a partial recanalization which allows to visualize the vessel distal to the occlusion. This allows to ascertain the wire position in the lumen of the artery.

The catheter as described for any of the embodiments of FIGS. 11 to 20 has, for example, a length of 1403 mm and an outer diameter of less than about 1 mm. The catheter is connected to the pressure means which comprises an infusion pump or an injector able to deliver at least 20 mL/min of constant flow rate. The infusion pump is set at a maximum of 700 PSI or about 50 ATM or about 50×101,325 Pa. The pump or the injector are filled with saline at room temperature. The saline is made with 1 L of water+9 g of NaCl (0.9%).

After connection to the pump, the catheter is flushed and advanced over the wire and placed in the very distal part of the guide catheter.

Through the catheter, the saline infusion is provided at a constant flow rate of 20 mL/min and at a pressure of about 40 ATM or about 40×101325 Pa. The saline exits the catheter through the at least 4 lateral holes so that the jets F are perpendicular to the longitudinal axis of the catheter and thus of the artery.

The catheter is passed slowly through the occlusion T and pulled back in the guiding while maintaining a substantially constant infusion rate. The passage is repeated up to 4 times.

Thereafter, the remainder of the primary PCI is left to the operator's discretion.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A catheter system for performing destruction of a body obstruction in a body vessel of a live being, the catheter system comprising a catheter shaft comprising a proximal end and a distal end, defining a longitudinal axis, including an outer tubular member having an outer wall and at least one inner tubular member disposed within the outer tubular member having an inner wall; a first fluid lumen defined between the inner tubular member and the outer tubular member, said inner tubular member and said outer tubular member being sealed together at said distal end to form a common distal end, and at least one second lumen defined by the at least one inner tubular member, said inner tubular member being open at said distal end; one or more fluid exit openings located at a distal end region of the catheter extending through said outer wall of the outer tubular member from an inner surface of the outer tubular member to an outer surface of the outer tubular member and upstream from said distal end, and configured to permit fluid to exit outside from the catheter from the first fluid lumen; fluid pressure means located external of the catheter upstream from the proximal end for delivering said fluid in the first fluid lumen at a pressure range predetermined to cause destruction of said obstruction.

2. The catheter system of claim 1, further comprising an elongate member advanceable through the second lumen of the catheter.

3. The catheter system of claim 2, wherein the elongate member comprises a temperature sensor positioned on a distal end portion of the elongate member.

4. The catheter system of claim 3 wherein the temperature sensor on the distal end portion of the elongate member is positionable downstream of the distal end of the catheter to measure temperature in the blood vessel.

5. The catheter system of claim 1, wherein the one or more fluid exit openings extend substantially perpendicularly to said longitudinal axis through said outer wall of the outer tubular member.

6. The catheter system of claim 1, wherein the one or more fluid exit openings are configured to generate a jet of fluid exiting the catheter and at a pressure sufficient to cause mechanical destruction of the body obstruction.

7. The catheter system of claim 1, wherein the one or more fluid exit openings include at least one set of four fluid exit openings equidistantly spaced circumferentially around the outer tubular member.

8. The catheter system of claim 5, wherein the one or more fluid exit openings include at least two sets of four fluid exit openings equidistantly spaced circumferentially around the outer tubular member.

9. The catheter system of claim 1, wherein the fluid exit opening(s) have a diameter ranging between about 70 microns (0.070 millimeters) and about 100 microns (0.100 millimeters) and said fluid pressure at the entrance of said catheter or at the vicinity of at least one fluid exit opening ranges between about, or more than 30×101325 Pa or 30 ATM and about 50×101325 Pa or 50 ATM.

10. The catheter system of claim 1, wherein one or more fluid inner holes are located at the distal end region of the catheter, and are configured to permit fluid to pass from the first fluid lumen into the second lumen and said one or more fluid inner holes extend through a wall of the inner tubular member from an outer surface of the inner tubular member to an inner surface of the inner tubular member.

11. The catheter system of claim 10, wherein the one or more fluid inner holes have a diameter ranging between about 100 micrometers and about 300 micrometers.

12. The catheter system of claim 1, wherein the elongate catheter shaft includes an elongated reduced diameter region extending distal of the one or more fluid exit openings to the distal end of the elongate catheter shaft.

13. The catheter system of claim 1, wherein a first temperature sensor is positioned within the first fluid lumen of the catheter shaft proximate the one or more fluid exit openings, the first temperature sensor configured to be in direct contact with the fluid within the lumen to measure a temperature of the fluid exiting the lumen through the one or more fluid exit openings.

14. The catheter system of claim 13, further comprising a second temperature sensor positioned on an exterior of the elongated reduced diameter region proximate the distal end of the elongate catheter shaft.

15. The catheter system of claim 14, wherein the second temperature sensor is positioned at least 4 centimeters distal of the one or more fluid exit openings.

16. The catheter system of claim 1, further comprising:
an elongate member comprising a guidewire advanceable through said inner tubular member, and wherein said catheter is selected from an Over The Wire (OTW) catheter and a Single Operator Exchange (SOE) catheter.

17. The catheter system of claim 16, wherein the guidewire comprises a temperature sensor positioned on a distal end portion of the guidewire to measure a temperature of a blood/fluid mixture in the body lumen distal of the one or more fluid exit openings.

18. The catheter system of claim 1, wherein the catheter comprises at least one pressure sensor in the vicinity of at least one fluid exit opening.

19. The catheter system of claim 1 wherein the fluid is a liquid selected from a saline and an aqueous solution compatible with blood.

20. The catheter system of claim 19, wherein the saline solution or the aqueous solution compatible with blood comprises at least one clot or thrombosis dissolution aid.

21. A catheter system for performing destruction of a body obstruction in a body vessel of a live being, the catheter system comprising a catheter shaft comprising a proximal end and a distal end, defining a longitudinal axis, including an outer tubular member having an outer wall and at least one inner tubular member disposed within the outer tubular member having an inner wall; a first fluid lumen defined between the inner tubular member and the outer tubular member, said inner tubular member and said outer tubular member being sealingly secured together at said distal end to form a common distal end, and at least one second lumen defined by the at least one inner tubular member, said inner tubular member being open at said distal end; one or more fluid exit openings located at a distal end region of the catheter extending through said outer wall of the outer tubular member from an inner surface of the outer tubular member to an outer surface of the outer tubular member and upstream from said distal end, and configured to permit fluid to exit outside from the catheter from the first fluid lumen; fluid pressure means located external of the catheter upstream from the proximal end for delivering said fluid in the first fluid lumen at a pressure range predetermined to cause destruction of said obstruction, wherein the fluid exit opening(s) have a diameter ranging between about 50 microns (0.050 millimeters) and about 110 microns (0.110 millimeters) and said fluid pressure at the entrance of said catheter or at the vicinity of at least one fluid exit opening ranges between about 20×101325 Pa or 20 ATM and about 50×101325 Pa or 50 ATM.

22. The catheter system of claim 21, wherein the fluid is a liquid selected from a saline and an aqueous solution compatible with blood.

23. The catheter system of claim 22, wherein the saline solution or the aqueous solution compatible with blood comprises at least one clot or thrombosis dissolution aid.

24. A method of performing destruction of a body obstruction in a body vessel of a live being, the method comprising:
advancing a catheter to a desired location comprising said obstruction within the body vessel, the catheter including a catheter shaft, defining a longitudinal axis, including an outer tubular member having an outer wall and at least one inner tubular member disposed within the outer tubular member having an inner wall; a first fluid lumen defined between the inner tubular member and the outer tubular member, said inner tubular member and said outer tubular member being sealed together at said distal end to form a common distal end, and at least one second lumen defined by the at least one inner tubular member, said inner tubular member being open at said distal end; one or more fluid exit openings located at a distal end region of the catheter extending through said outer wall of the outer tubular member from an inner surface of the outer tubular member to an outer surface of the outer tubular member and upstream from said distal end, and configured to permit fluid to exit outside from the catheter from the first fluid lumen; and fluid pressure means located external of the catheter upstream from the proximal end for delivering said fluid in the first fluid lumen at a pressure range predetermined to cause destruction of said obstruction providing a delivery of a fluid through the first fluid lumen to a distal end region of the catheter and at a pressure range predetermined to exit said fluid at a pressure and for a period of time causing destruction of said obstruction.

25. The method of claim 24, wherein the catheter comprises at least one set of four fluid exit openings located at the distal end region of the catheter equidistantly spaced circumferentially around the outer tubular member.

26. The method of claim 24, wherein the catheter comprises two sets of four fluid exit openings located at the distal end region of the catheter equidistantly spaced circumferentially around the outer tubular member.

27. The method of claim 24, wherein the advancing step of said catheter within said body step comprises using an elongate member.

28. The method of claim 27, wherein said elongate member is a guidewire, and wherein said catheter is selected from an Over The Wire (OTW) catheter and a Single Operator Exchange (SOE) catheter.

29. The method of claim 24, wherein said catheter is provided with a temperature probe, said method comprising measuring with said temperature sensor the temperature of the fluid exiting the catheter or of the blood ahead of the distal end of the catheter.

30. The method of claim 24, further comprising:
providing at least one temperature sensor on the distal end of the elongate member and positioning the elongate member to a location distal of the catheter for measuring the temperature of the mixture of the fluid and the blood distal of the catheter.

31. The method of claim 24, wherein the catheter includes one or more fluid inner holes located at the distal end region of the catheter in the vicinity of at least one said fluid exit opening, the one or more fluid inner holes configured on the inner tube to permit the fluid to pass from the first fluid lumen into the second lumen; and repositioning the elongate member to a location in front of one said fluid inner hole to measure the temperature of the fluid in the vicinity of the fluid exiting the catheter.

32. The method of claim 24, comprising providing said fluid exit opening(s) with a diameter ranging between about 50 microns (0.050 millimeters) and about 110 microns (0.110 millimeters) and said fluid pressure at the entrance of said catheter or at the vicinity of at least one fluid exit opening ranges between about 20×101,325 Pa or 20 ATM and about 50×101,325 Pa or 50 ATM.

33. The method of claim 24, comprising providing said fluid exit opening(s) with a diameter ranging between about 70 microns (0.070 millimeters) and about 100 microns (0.100 millimeters) and said fluid pressure at the entrance of said catheter or at the vicinity of at least one fluid exit opening ranges between about or at least 30×101,325 Pa or 30 ATM and about 50×101,325 Pa or 50 ATM.

34. The method of claim 24, wherein the catheter comprises at least one pressure sensor in the vicinity of at least one fluid exit opening, said method comprising measuring the pressure of said fluid at the vicinity of said fluid exit opening and correcting the fluid pressure value injected within the fluid lumen.

35. The method of claim 24 comprising providing a fluid as a liquid selected from a saline and an aqueous solution compatible with blood.

36. The method of claim 35, wherein the saline solution or the aqueous solution compatible with blood comprises at least one clot or thrombosis dissolution aid.

* * * * *